(12) United States Patent
Gamache et al.

(10) Patent No.: US 8,791,154 B2
(45) Date of Patent: Jul. 29, 2014

(54) HIGH CONCENTRATION OLOPATADINE OPHTHALMIC COMPOSITION

(75) Inventors: Daniel A. Gamache, Arlington, TX (US); Laman Alani, Fort Worth, TX (US); Malay Ghosh, Fort Worth, TX (US); Francisco Javier Galán, Barcelona (ES); Núria Carreras Perdiguer, Barcelona (ES); Onkar N. Singh, Arlington, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 1 day.

(21) Appl. No.: 13/475,607

(22) Filed: May 18, 2012

(65) Prior Publication Data
US 2012/0295967 A1   Nov. 22, 2012

Related U.S. Application Data

(60) Provisional application No. 61/487,789, filed on May 19, 2011, provisional application No. 61/548,957, filed on Oct. 19, 2011.

(51) Int. Cl.
| | | |
|---|---|---|
| *A61K 31/335* | (2006.01) | |
| *A61K 47/48* | (2006.01) | |
| *C08B 37/16* | (2006.01) | |
| *C08L 5/16* | (2006.01) | |
| *A61K 9/08* | (2006.01) | |
| *A61K 9/00* | (2006.01) | |
| *A61K 47/32* | (2006.01) | |

(52) U.S. Cl.
CPC ......... *A61K 31/335* (2013.01); *A61K 47/48969* (2013.01); *C08B 37/0015* (2013.01); *C08L 5/16* (2013.01); *A61K 47/32* (2013.01); *A61K 9/08* (2013.01); *A61K 9/0048* (2013.01)
USPC .......................................... 514/450; 514/449

(58) Field of Classification Search
USPC ............................................... 514/449, 450
See application file for complete search history.

(56) References Cited

U.S. PATENT DOCUMENTS

| | | |
|---|---|---|
| 3,767,788 A | 10/1973 | Rankin |
| 3,843,782 A | 10/1974 | Krezanoski et al. |
| 3,856,919 A | 12/1974 | Rankin |
| 3,931,319 A | 1/1976 | Green et al. |
| 3,947,573 A | 3/1976 | Rankin |
| 4,027,020 A | 5/1977 | Green et al. |
| 4,120,949 A | 10/1978 | Bapatla et al. |
| 4,283,393 A | 8/1981 | Field et al. |
| 4,407,791 A | 10/1983 | Stark |
| 4,470,965 A | 9/1984 | Wolf et al. |
| 4,525,346 A | 6/1985 | Stark |
| 4,836,986 A | 6/1989 | Ogunbiyi et al. |
| 4,923,693 A | 5/1990 | Michalos |
| 5,037,647 A | 8/1991 | Chowhan et al. |
| 5,068,225 A | 11/1991 | Pennell et al. |
| 5,116,863 A | 5/1992 | Oshima et al. |
| 5,134,127 A | 7/1992 | Stella et al. |
| 5,141,961 A | 8/1992 | Coapman |
| 5,300,287 A | 4/1994 | Park |
| 5,376,645 A | 12/1994 | Stella et al. |
| 5,472,954 A | 12/1995 | Loftsson |
| 5,591,426 A | 1/1997 | Dabrowski et al. |
| 5,597,559 A | 1/1997 | Olejnik et al. |
| 5,624,962 A | 4/1997 | Takeuchi et al. |
| 5,641,805 A * | 6/1997 | Hayakawa et al. ........... 514/450 |
| 5,874,414 A | 2/1999 | Haseloff et al. |
| 5,874,418 A * | 2/1999 | Stella et al. .................... 514/58 |
| 5,888,493 A | 3/1999 | Sawaya |
| 6,153,746 A | 11/2000 | Shah et al. |
| 6,280,745 B1 | 8/2001 | Flore et al. |
| 6,407,079 B1 | 6/2002 | Muller et al. |
| 6,511,949 B1 | 1/2003 | Nitta et al. |
| 6,828,356 B2 | 12/2004 | Su et al. |
| 6,995,186 B2 * | 2/2006 | Castillo et al. ................ 514/450 |
| 7,074,424 B2 | 7/2006 | Avila et al. |
| 7,147,844 B2 | 12/2006 | Hamano et al. |
| 7,429,602 B2 | 9/2008 | Trach et al. |
| 7,635,773 B2 | 12/2009 | Antle |
| 2002/0006443 A1 | 1/2002 | Curatolo et al. |
| 2002/0150616 A1 | 10/2002 | Vandecruys |
| 2003/0170309 A1 | 9/2003 | Babcock et al. |
| 2004/0198828 A1 * | 10/2004 | Abelson et al. ............... 514/571 |
| 2005/0004074 A1 | 1/2005 | Lyons et al. |
| 2005/0191270 A1 | 9/2005 | Gruening et al. |

(Continued)

FOREIGN PATENT DOCUMENTS

| | | |
|---|---|---|
| CA | 2 391 076 | 5/2001 |
| EP | 1 004 309 | 5/2000 |

(Continued)

OTHER PUBLICATIONS

Chigbu, "The management of allergic eye disease in primary eye care", Contact Lens & Anterior Eye, 32, pp. 260-272, 2009.
Chigbu, "The pathophysiology of ocular allergy: A review", Contact Lens & Anterior Eye, 32, pp. 3-15, 2009.
Ciprandi et al., "Cetirizine reduces inflammatory cell recruitment and ICAM-1 (or CD54) expression on conjunctival epithelium in both early- and late-phase reactions after allergen-specific challenge", J Allergy Clin Immunol, vol. 95, No. 2, pp. 612-621, Feb. 1995.
Du Buske, "Clinical comparison of histamine H1-receptor antagonist drugs", J Allergy Clin Immunol, vol. 98, No. 6, part 3, pp. S307-S318, Dec. 1996.

(Continued)

*Primary Examiner* — My-Chau T Tran
(74) *Attorney, Agent, or Firm* — Scott A. Chapple

(57) ABSTRACT

The present invention is an ophthalmic composition containing a relatively high concentration of olopatadine. The composition is typically an ophthalmic aqueous solution containing relatively high concentrations of olopatadine solubilized within the solution. The composition is preferably capable of providing enhanced relief from symptoms of ocular allergic conjunctivitis, particularly late phase symptoms of ocular allergic conjunctivitis.

27 Claims, 5 Drawing Sheets

(56) References Cited

U.S. PATENT DOCUMENTS

| | | | |
|---|---|---|---|
| 2005/0244472 A1 | 11/2005 | Hughes et al. | |
| 2006/0210645 A1 | 9/2006 | Du Mee et al. | |
| 2007/0020336 A1 | 1/2007 | Loftsson et al. | |
| 2008/0132444 A1 | 6/2008 | Li et al. | |
| 2009/0118262 A1 | 5/2009 | Rohrs et al. | |
| 2009/0232763 A1 | 9/2009 | Kabra et al. | |
| 2009/0239842 A1 | 9/2009 | Trach et al. | |
| 2010/0240625 A1 | 9/2010 | Abelson et al. | |
| 2010/0249062 A1 | 9/2010 | Matsumura et al. | |
| 2010/0324031 A1 | 12/2010 | Kabra | |
| 2011/0082145 A1* | 4/2011 | Schneider et al. | 514/235.2 |
| 2012/0015953 A1* | 1/2012 | Beauregard et al. | 514/250 |

FOREIGN PATENT DOCUMENTS

| | | |
|---|---|---|
| EP | 0862414 | 12/2001 |
| EP | 0998304 | 8/2003 |
| EP | 1 231 920 | 2/2007 |
| EP | 1 994 931 | 11/2008 |
| GB | 2169508 | 7/1986 |
| JP | 2001-158750 | 6/2001 |
| WO | 88/08709 | 11/1988 |
| WO | 90/04971 | 5/1990 |
| WO | 91/09523 | 7/1991 |
| WO | 96/39147 | 12/1996 |
| WO | 01/54687 | 8/2001 |
| WO | 03/013481 | 2/2003 |
| WO | 2006/011044 | 2/2006 |
| WO | 2008/015695 | 2/2008 |
| WO | 2009/003199 | 12/2008 |
| WO | 2010/107689 | 9/2010 |

OTHER PUBLICATIONS

Fukuda et al., "Critical role of IgE-dependent mast cell activiation in a murine model of allergic conjunctivitis", J Allergy Clin Immunol, vol. 124, No. 4, 827-833.e2, Oct. 2009.

International Search Report for corresponding PCT/US2012/038663 with mailing date Jul. 25, 2012.

International Written Opinion for corresponding PCT/US2012/038663 with mailing date Jul. 25, 2012.

Izushi et al., "The role of histamine H1 receptors in late-phase reaction of allergic conjunctivitis", European Journal of Pharmacology, 440:79-82, 2002.

Leonardi and Abelson, "Double-Masked, Randomized, Placebo-Controlled Clinical Study of the Mast Cell-Stabilizing Effects of Treatment with Olopatadine in the Conjunctival Allergen Challenge Model in Humans", Clinical Therapeutics, vol. 25, No. 10, pp. 2539-2552, 2003.

Ozaki et al., "Mast-cell activation augments the late phase reaction in experimental immune-mediated blepharoconjunctivitis", Graefe's Arch Clin Exp Ophthalmol, 241:394-402, 2003.

Ueta et al., letter to editor, "Development of eosinophilic conjunctival inflammation at late-phase reaction in mst cell-deficient mice", J Allergy Clin Immunol, pp. 476-478, Aug. 2007.

Vogelson et al., "Preclinical and Clinical Antiallergic Effect of Olopatadine 0.2% Solution 24 Hours after Topical Ocular Administration", Allergy and Asthma Proc., vol. 25, No. 1, pp. 69-75, Jan.-Feb. 2004.

Yanni et al., "The In Vitro and In Vivo Ocular Pharmacology of Olopatadine (AL-4943A), an Effective Anti-Allegic/Antihistaminic Agent", Journal of Ocular Pharmacology and Therapeutics, vol. 12, No. 4, 1996.

International Preliminary Report on Patentability for corresponding PCT/US2012/038663 with mailing date Nov. 28, 2013.

* cited by examiner

HIGH CONCENTRATION OLOPATADINE OPHTHALMIC COMPOSITION

CROSS-REFERENCE TO RELATED APPLICATION

The present application claims priority based on U.S. Provisional Patent Application Ser. No. 61/487,789 filed May 19, 2011 and U.S. Provisional Patent Application Ser. No. 61/548,957 filed Oct. 19, 2011.

TECHNICAL FIELD OF THE INVENTION

The present invention relates to an ophthalmic composition containing a relatively high concentration of olopatadine. More particularly, the present invention relates to an ophthalmic aqueous solution containing a relatively high concentration of solubilized olopatadine wherein the solution is capable of providing enhanced relief from symptoms of ocular allergic disorders (e.g., conjunctivitis) in the early phase, the late phase or preferably both phases.

BACKGROUND OF THE INVENTION

Individuals suffering from allergic conjunctivitis experience symptoms such as ocular irritation, itchiness, redness and the like. It has been found that these symptoms are significantly reduced using topical ophthalmic solutions containing olopatadine. Such solutions are sold under the tradenames PATANOL® and PATADAY®, which are both commercially available from Alcon Laboratories, Inc., Fort Worth, Tex.

These marketed solutions were generally believed to be the most efficacious products known for addressing symptoms of allergic conjunctivitis. Surprisingly, and as discussed further below, it has been discovered that relatively high concentration solutions of olopatadine provide significantly improved reduction of late phase ocular allergic conjunctivitis symptoms in addition to relief from early phase symptoms. Even more surprising, it has been discovered that such high concentrations of olopatadine also provide significantly improved reduction of redness in the early phase. Further, it has been discovered that enhanced relief from these early and late phase symptoms can be achieved through once a day dosing of relatively high concentration olopatadine solution as opposed to greater dosing frequencies.

The discovery of improved reduction of early and late phase symptoms is quite significant and desirable for individuals suffering from allergic conjunctivitis. Generally, these discoveries can provide patients greater relief from itching and provide better aesthetic appearance to the eye. Further, avoiding more frequent dosing is more convenient for patients and helps assure better compliance. Further yet, improved early prevention and/or reduction of redness is particularly desirable since patients generally have a desire to keep as much redness out of their eyes as possible.

The discovery that relatively high concentration solutions of olopatadine can relieve late phase ocular allergic conjunctivitis symptoms provides hope to sufferers of ocular allergic conjunctivitis that a single dose of olopatadine per day could provide a substantial degree of full day relief from their symptoms. However, the development of a multi-dose ophthalmic solution that includes high concentrations of olopatadine necessary to achieve desired levels of efficacy is extremely difficult and complex.

Solubilizing high concentrations of olopatadine in a stable manner has proven difficult by itself. Olopatadine, by itself, is only soluble in water (pH about 7.0) at room temperature up to a concentration of about 0.18 w/v %. However, it is desirable to achieve solubilization of much higher concentrations of olopatadine in an effort to treat late phase allergic conjunctivitis.

Solubilizing such higher concentrations of olopatadine has proven difficult. As one example, excipients such as polyethylene glycol (PEG) 400 and polyvinylpyrrolidone (PVP), when used at reasonably desirable concentrations, have proven incapable, alone or in combination, of solubizing sufficient concentrations of olopatadine in compositions having approximately neutral pH. Thus, innovation is required to solubilize a sufficient concentration of olopatadine.

In the process of such innovation, is has been discovered that higher molecular weight PEGs such as PEG 6000 can significantly enhance solubility of olopatadine. However, such PEGs cause risk of discomfort when administered to humans. It has also been discovered that cyclodextrins, such as hydroxypropyl-γ-cyclodextrin, hydroxypropyl-β-cyclodextrin and sulfoalkyl ether-β-cyclodextrin, have the ability to solubilize significantly higher concentrations of olopatadine. However, use of undesirably high concentrations of cyclodextrins has been found to reduce olopatadine efficacy and/or preservation efficacy of solutions. As such, still further innovation was needed to create a desirable olopatadine formulation that not only solubilized sufficient amounts of olopatadine, but also allowed the formulation to achieve other desirable pharmaceutical characteristics.

Thus, the present invention is directed at an ophthalmic composition that can provide high concentrations of olopatadine topically to the eye. Further, the present invention is directed to such a composition wherein the olopatadine is solubilized in solution in a stable manner, the composition exhibits consistent efficacy against late phase symptoms of allergic conjunctivitis, the composition exhibits sufficient antimicrobial activity to provide desired levels of preservation efficacy or any combination thereof.

SUMMARY OF THE INVENTION

The present invention is directed to an ophthalmic composition for treatment of allergic conjunctivitis. The composition will include a relatively high concentration of olopatadine, preferably at least 0.67 w/v % olopatadine, preferably dissolved in solution. The composition will typically include a cyclodextrin, and more particularly, a γ-cyclodextrin derivative and/or a β-cyclodextrin derivative to aid in solubilizing the olopatadine. The cyclodextrin derivative is preferably hydroxypropyl-γ-cyclodextrin (HP-γ-CD), hydroxypropyl-β-cyclodextrin (HP-β-CD), sulfoalkyl ether β-cyclodextrin (SAE-β-CD)(e.g., sulfobutyl ether β-cyclodextrin (SBE-β-CD)), or a combination thereof. The composition will typically include a lactam polymer (e.g., polyvinylpyrrolidone (PVP)) to aid in the solubilization of the olopatadine. The composition will also typically include a polyether (e.g., polyethylene glycol (PEG)) for enhancing solubility and/or aiding in achieving the desired tonicity. It is generally desirable for the composition to be disposed in an eyedropper, have a pH of 5.5 to 8.0, to have an osmolality of 200 to 450, to have a viscosity of 10 to 200 cps or any combination thereof. The composition will also typically include a preservative to allow the composition to achieve United States and/or European Pharmacopeia preservation standards. Preferred preservatives include a polymeric quaternary ammonium compound, such as polyquaternium-1, and benzalkonium chloride. The composition also typically includes borate and/or polyol to aid in achieving desired preservation.

The present invention also contemplates a method of treating ocular allergy symptoms. The method will include topically applying a composition having a defined combination of the characteristics described above to an eye of a human. This step of topically applying the composition preferably includes dispensing an eyedrop from an eyedropper.

DETAILED DESCRIPTION OF THE INVENTION

Figure 1:
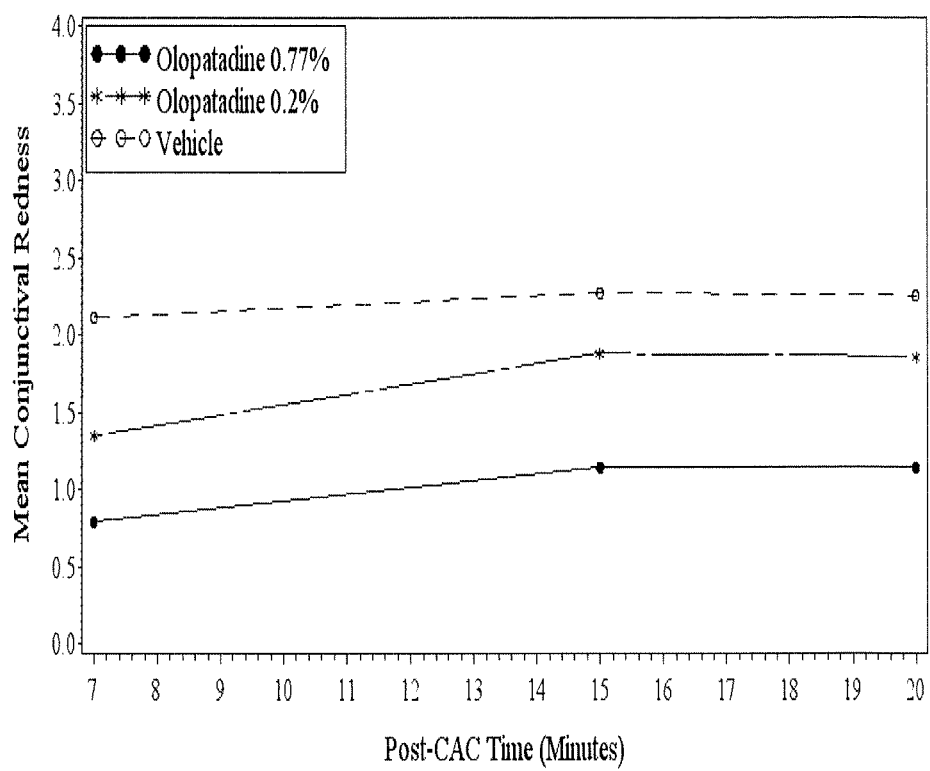
FIG. 1 is a graph of mean conjunctival redness determined by a conjunctival allergen challenge (CAC) at 27 minutes.

The present invention is predicated upon the provision of an ophthalmic composition for treatment of allergic conjunctivitis. The ophthalmic composition is preferably an aqueous solution. The ophthalmic composition includes a relatively high concentration of olopatadine solubilized in aqueous solution. The ophthalmic composition also includes a unique set of excipients for solubilizing the olopatadine while maintaining comfort of the composition and/or efficacy of the composition in treating symptoms associate with allergic conjunctivitis, particularly symptoms associated with late phase allergic conjunctivitis. Preferably, the composition exhibits improved late phase efficacy in reducing ocular itching, ocular redness or both. The composition also preferably exhibits improved early phase efficacy in reducing ocular redness relative to vehicle and/or relative to lower concentrations of olopatadine. In a preferred embodiment, the ophthalmic composition is a multi-dose ophthalmic composition that also exhibits a required degree of preservation efficacy.

Unless indicated otherwise, all component amounts (i.e., concentrations) are presented on a weight volume percent (w/v %) basis and all references to concentrations of olopatadine are to olopatadine free base.

Olopatadine is a known compound that can be obtained by the methods disclosed in U.S. Pat. No. 5,116,863, the entire contents of which are hereby incorporated by reference in the present specification for all purposes. The formulation of the present invention contains at least 0.50%, more typically at least 0.55%, more typically at least 0.6% or 0.65%, even more typically at least 0.67% or 0.68%, still more typically at least 0.7%, possibly at least 0.75% and even possibly at least 0.85% but typically no greater than 1.5% more typically no greater than 1.0%, still more typically no greater than 0.8%, possibly no greater than 0.75% and even possibly no greater than 0.72% of olopatadine where concentrations of olopatadine typically represent concentrations of olopatadine in free base form if the olopatadine is added to the composition as a salt. These lower limits of concentrations of olopatadine are particularly important since it has been found that efficacy of olopatadine in aqueous ophthalmic solutions in reducing late phase allergy symptoms and enhanced reduction of early phase redness begins to show improvement at concentrations greater than 0.5 w/v % of olopatadine and begins to show statistically significant improvements in reducing late phase allergy symptoms at concentrations of about 0.7 w/v % olopatadine and above (e.g., at least 0.65 w/v %, at least 0.67 w/v % or at least 0.68 w/v %). Most preferably, the concentration of the olopatadine in the composition is 0.7 w/v %.

Generally, olopatadine will be added in the form of a pharmaceutically acceptable salt. Examples of the pharmaceutically acceptable salts of olopatadine include inorganic acid salts such as hydrochloride, hydrobromide, sulfate and phosphate; organic acid salts such as acetate, maleate, fumarate, tartrate and citrate; alkali metal salts such as sodium salt and potassium salt; alkaline earth metal salts such as magnesium salt and calcium salt; metal salts such as aluminum salt and zinc salt; and organic amine addition salts such as triethylamine addition salt (also known as tromethamine), morpholine addition salt and piperidine addition salt. The most preferred form of olopatadine for use in the solution compositions of the present invention is the hydrochloride salt of (Z)-11-β-dimethylaminopropylidene)-6,11-dihydrodibenz-[b,e]oxepin-2-acetic acid. When olopatadine is added to the compositions of the present invention in this salt form, 0.77% olopatadine hydrochloride is equivalent to 0.7% olopatadine free base, 0.88% olopatadine hydrochloride is equivalent to 0.8% olopatadine free base, and 0.99% olopatadine hydrochloride is equivalent to 0.9% olopatadine free base.

Generally, it is preferred that the entire concentration of olopatadine is dissolved in the composition as a water based or aqueous solution. However, it is contemplated that olopatadine could be only partially dissolved. For example, a portion of the olopatadine could be in solution with the remainder being in suspension.

The composition of the present invention also preferably includes cyclodextrin derivative and more preferably β-cyclodextrin derivative, γ-cyclodextrin derivative or both to aid in solubilizing the olopatadine (i.e., as a solubilizer). The β-cyclodextrin derivative, γ-cyclodextrin derivative or combination thereof is typically present in the composition at a concentration that is at least 0.5% w/v, more typically at least 1.0% w/v and even possibly at least 1.3% w/v, but is typically no greater than 4.0% w/v, typically no greater than 3.2% w/v and even possibly no greater than 2.8% w/v. Preferably, the total concentration of cyclodextrin is from 0.9 w/v % to 3.2 w/v %.

The specific amount of β-cyclodextrin derivative, γ-cyclodextrin derivative or combination thereof in a particular composition will typically depend upon the type or combination of types of derivatives used. One particularly desirable β-cyclodextrin derivative is a hydroxy alkyl-β-cyclodextrin such as hydroxypropyl-β-cyclodextrin (HP-β-CD). One particularly desirable γ-cyclodextrin derivative is a hydroxy alkyl-γ-cyclodextrin such as hydroxypropyl-γ-cyclodextrin (HP-γ-CD). Another particularly desirable β-cyclodextrin derivative is sulfoalkyl ether-β-cyclodextrin (SAE-β-CD), particularly sulfobutyl ether-β-cyclodextrin (SBE-β-CD). It is contemplated that a combination of hydroxypropyl-β-cyclodextrin, hydroxypropyl-γ-cyclodextrin and/or sulfoalkyl ether-β-cyclodextrin derivative may be employed in a single composition, but it is typically desirable to use only one of the three as the sole or substantially the sole (i.e., at least 90% by weight of the cyclodextrin component) cyclodextrin derivative.

When HP-β-CD is employed as the sole or substantially sole β-cyclodextrin derivative, it is typically present in the composition at a concentration that is at least 0.5% w/v, more typically at least 1.0% w/v and even more typically at least 1.3% w/v, but is typically no greater than 3.0% w/v, typically no greater than 2.2% w/v and is typically no greater than 1.7% w/v. When HP-γ-CD is employed as the sole or substantially sole γ-cyclodextrin derivative, it is typically present in the composition at a concentration that is at least 0.5% w/v, more typically at least 1.0% w/v and even more typically at least 1.3% w/v, but is typically no greater than 3.0% w/v, typically no greater than 2.2% w/v and is typically no greater than 1.7% w/v. When SAE-β-CD is employed as the sole or substantially sole β-cyclodextrin derivative, it is typically present in the composition at a concentration that is at least 0.3% w/v, more typically at least 0.7% w/v and even more typically at least 0.9% w/v, but is typically no greater than 2.4% w/v, typically no greater than 1.5% w/v and is typically no greater than 1.1% w/v.

HP-β-CD is a commodity product and pharmaceutical grades of HP-β-CD can be purchased from a variety of sources, for example, from SIGMA ALDRICH, which has its corporate headquarters in St. Louis, Mo. or ASHLAND SPECIALTY INGREDIENTS, headquartered in Wayne, N.J. HP-γ-CD is a commodity product and pharmaceutical grades of HP-γ-CD can be purchased from a variety of sources, for example, from SIGMA ALDRICH, which has its corporate headquarters in St. Louis, Mo. or ASHLAND SPECIALTY INGREDIENTS, headquartered in Wayne, N.J. SAE-β-CD can be formed based upon the teachings of U.S. Pat. Nos. 5,134,127 and 5,376,645, which are incorporated herein by reference for all purposes. It is generally preferred, however, to use purified SAE-β-CD. Purified SAE-β-CD is preferably formed in accordance with the teachings of U.S. Pat. Nos. 6,153,746 and 7,635,773. Purified SAE-β-CD is commercially available under the tradename CAPTISOL® from CyDex Pharmaceuticals, Inc., Lenexa, Kans.

With regard to γ-cyclodextrin derivative and β-cyclodextrin derivative in the composition of the present invention, it has been found that undesirably high concentrations of γ-cyclodextrin derivative and/or β-cyclodextrin derivative can significantly interfere with preservation efficacy of the compositions, particularly when benzalkonium chloride and/or polymeric quaternary ammonium compound are employed as preservation agents. Thus, lower concentrations of γ-cyclodextrin derivative and/or β-cyclodextrin derivative are typically preferred. Advantageously, it has also been found, however, that the ability of the γ-cyclodextrin derivative and β-cyclodextrin derivatives in solubilizing olopatadine is very strong and relatively low concentrations of γ-cyclodextrin derivative and/or β-cyclodextrin derivative can solubilize significant concentrations of olopatadine in aqueous solution. As such, more desirable and reasonable concentrations of additional solubilizing agent can be used to aid in solubilizing the desired amounts of olopatadine.

Further, it has been found that a composition formed using a combination of solubilizing agents such as polyvinylpyrrolidone, tyloxapol, polyethylene glycol and others to solubilize relatively high concentrations of olopatadine in the absence of γ-cyclodextrin derivative and/or β-cyclodextrin derivative will typically lack long term stability or shelf life. It has been found that such a composition will typically begin to precipitate after undesirably short periods of time. Thus, it is important to employ the γ-cyclodextrin derivative and/or β-cyclodextrin derivative in combination with one or more additional solubilizers.

As such, the ophthalmic composition of the present invention includes at least one solubilizing agent (i.e., solubilizer), but possibly two or more solubilizing agents, in addition to cyclodextrin. The additional solubilizing agents can include surfactants such as castor oil, polysorbate or others. Preferably, the additional solubilizing agent[s] includes one or more polymers. One preferred polymer for aiding in solubilizing the olopatadine is lactam polymer. Another preferred polymer for aiding in solubilizing the olopatadine is polyether.

As used herein, the phrase "lactam polymer" refers to any polymer formed from more than one lactam monomer. The lactam polymer is typically present in the composition at a concentration that is at least 1.0% w/v, more typically at least 3.0% w/v and even more typically at least 3.7% w/v, but is typically no greater than 8.0% w/v, typically no greater than 5.0% w/v and is typically no greater than 4.3% w/v. Polyvinylpyrrolidone (PVP) is the most preferred lactam polymer and can be the only or substantially the only lactam polymer. Thus, in a preferred embodiment, the lactam polymer consists or consists essentially of only PVP. The average molecular weight of the lactam polymer, particularly when it is PVP, is at least 20,000, more typically at least 46,000 and even more typically at least 54,000 but is typically no greater than 90,000, more typically no greater than 70,000 and still more typically no greater than 62,000. One preferred PVP is sold under the tradenames PLASDONE® K29/32 or K30, which have an average molecular weight of approximately 50,000 and are commercially available from ASHLAND SPECIALTY INGREDIENTS, headquartered in Wayne, N.J., USA.

The polyether can aid in the solubility of olopatadine in the composition and/or can provide tonicity to the composition (i.e., act as a tonicity agent). The polyether is typically present in the composition at a concentration that is at least 1.0% w/v, more typically at least 3.0% w/v and even more typically at least 3.7% w/v, but is typically no greater than 8.0% w/v, typically no greater than 5.0% w/v and is typically no greater than 4.3% w/v. Polyethylene glycol (PEG) is the most preferred polyether and can be the only or substantially the only polyether polymer. Thus in a preferred embodiment, the polyether consists or consist essentially of only PEG. The average molecular weight of the PEG will typically depend upon the particular solubility and particular tonicity desired for the composition. In a preferred embodiment, the average molecular weight of the polyether, particularly when it is PEG, is at least 200, more typically at least 320 and even more typically at least 380 but is typically no greater than 800, more typically no greater than 580 and still more typically no greater than 420. One preferred PEG is PEG400.

It may also be desirable for the ophthalmic composition of the present invention to include a viscosity enhancing agent in order to enhance residence time of the composition upon the cornea when the composition is topically administered. Examples of potentially suitable viscosity enhancing agent include, without limitation, carboxyvinyl polymer, galactomannan, hyaluronic acid, cellulosic polymer, any combination thereof or the like. In a preferred embodiment, the ophthalmic composition includes hydroxyethyl cellulose (HEC), hydroxylpropylmethyl cellulose (HPMC) or both. One preferred HEC is sold under the tradename NASTROSOL® 250HX, which is commercially available from Hercules Incorporated, Aqualon Division, Argyle, Tex. One preferred HPMC is sold under the tradename E4M 2910 and is commercially available from Dow Chemical, Midland, Mich.

The amounts and molecular weights of HPMC and/or HEC used in the composition will depend upon the viscosity, osmolality and other attributes to be achieved for the composition. As used herein, viscosity is measured by a Brookfield viscometer (LVDVI+, CP-42, 12 RPM and a temperature of 25° C.). In a preferred embodiment, the viscosity of the composition is at least 2.0 centipoise (cps), more typically at least 15 cps, even more typically at least 21 cps and even possibly at least 27 cps, but is typically no greater than 65 cps, typically no greater than 40 cps, more typically nor greater than 33 cps and even possibly no greater than 30 cps. Advantageously, and as further discussed below, viscosity within these ranges has been discovered to be more desirable for producing desired droplet sizes when the composition of the present invention is topically delivered from an eye dropper.

The preferred average molecular weight of HEC, when used, is typically in the range of 90,000 to 1,300,000 (e.g., approximately 1,000,000). The preferred average molecular weight of HPMC is typically in the range of 10,000 to 1,500,000 and more typically in the range of 189,000 to 688,000).

When HPMC is used alone, it is typically present in composition at a concentration that is at least 0.15% w/v, more typically at least 0.3% w/v and even more typically at least 0.5% w/v, but is typically no greater than 1.5% w/v, typically no greater than 1.0% w/v and is typically no greater than 0.7% w/v. When HEC is used alone, it is typically present in the composition at a concentration that is at least 0.1% w/v, more typically at least 0.25% w/v and even more typically at least 0.45% w/v, but is typically no greater than 1.4% w/v, typically no greater than 0.9% w/v and is typically no greater than 0.65% w/v. Advantageously, when HPMC and HEC are used to together, they may produce a synergistic viscosity effect which allows the use of low concentrations of these excipients to produce the desired viscosity of the compositions. When HPMC and HEC are used in combination, HPMC is typically present in composition at a concentration that is at least 0.05% w/v, more typically at least 0.1% w/v and even more typically at least 0.2% w/v, but is typically no greater than 1.0% w/v, typically no greater than 0.55% w/v and is typically no greater than 0.4% w/v. When HPMC and HEC are used in combination, HEC is typically present in composition at a concentration that is at least 0.02% w/v, more typically at least 0.06% w/v and even more typically at least 0.09% w/v, but is typically no greater than 0.6% w/v, typically no greater than 0.3% w/v and is typically no greater than 0.17% w/v. Notably, in at least some embodiments of the present invention, HPMC is a preferred viscosity enhancing agent since, as the data present below shows, it can also aid in solubilizing the olopatadine.

The composition can also include buffering agents and/or tonicity agents. Suitable tonicity-adjusting agents and/or buffering agents include, but are not limited to, mannitol, sodium chloride, glycerin, sorbitol, phosphates, borates, acetates and the like.

Borate is a highly preferred buffering agent and will typically be included in the composition of the present invention. As used herein, the term "borate" shall refer to boric acid, salts of boric acid, borate derivatives and other pharmaceutically acceptable borates, or combinations thereof. Most suitable are: boric acid, sodium borate, potassium borate, calcium borate, magnesium borate, manganese borate, and other such borate salts. Typically, when used, the borate is at least about 0.05 w/v %, more typically at least about 0.18 w/v % and even possibly at least about 0.27 w/v % of the ophthalmic composition and is typically less than about 1.0 w/v %, more typically less than about 0.75 w/v % and still more typically less than about 0.4 w/v %, and even possibly less than about 0.35 w/v % of the ophthalmic composition.

The composition of the present invention can also include polyol. As used herein, the term "polyol" includes any compound having at least one hydroxyl group on each of two adjacent carbon atoms that are not in trans configuration relative to each other. The polyol can be linear or cyclic, substituted or unsubstituted, or mixtures thereof, so long as the resultant complex is water soluble and pharmaceutically acceptable. Examples of such compounds include: sugars, sugar alcohols, sugar acids and uronic acids. Preferred polyols are sugars, sugar alcohols and sugar acids, including, but not limited to: mannitol, glycerin, xylitol, sorbitol and propylene glycol. It is contemplated that the polyol may be comprised of two or more different polyols.

When both borate and polyol are present in the composition, borate typically interacts with polyol, such as glycerol, propylene glycol, sorbitol and mannitol, or any combination thereof to form borate polyol complexes. The type and ratio of such complexes depends on the number of OH groups of a polyol on adjacent carbon atoms that are not in trans configuration relative to each other. It shall be understood that weight/volume percentages of the ingredients polyol and borate include those amounts whether as part of a complex or not. Advantageously, the borate and polyol can act as buffers and/or tonicity agents and can also aid in enhancing preservation efficacy of the composition.

In a preferred embodiment of the invention, the composition includes propylene glycol, glycerine or both. It has been found that γ-cyclodextrin derivatives and/or β-cyclodextrin derivatives tend to inhibit preservation efficacy within the formulations of the present invention, however, propylene glycol in the presence of borate appears to significantly limit this inhibition. Moreover, it has been found that glycerine often acts in a manner very similar to propylene glycol when used for aiding preservation. When used, propylene glycol, glycerine or a combination thereof is typically present in the composition at a concentration that is at least 0.4 w/v %, more typically at least 0.65 w/v % and even possibly at least 0.85 w/v % but is typically no greater than 5.0 w/v %, more typically no greater than 2.2 w/v % and even more typically no greater than 1.7 w/v %.

In a same or alternative preferred embodiment of the invention, the composition includes mannitol, sorbitol or both. Mannitol may also aid preservation of the composition of the present invention when used in the presence of borate. Moreover, it has been found that sorbitol often acts in a manner very similar to mannitol when used for aiding preservation. When used, mannitol, sorbitol or a combination thereof is typically present in the composition at a concentration that is at least 0.05 w/v %, more typically at least 0.2 w/v % and even possibly at least 0.4 w/v % but is typically no greater than 3.0 w/v %, more typically no greater than 1.0 w/v % and even more typically no greater than 0.5 w/v %.

The composition of the present invention typically includes a preservative. Potential preservatives include, without limitation, hydrogen peroxide, benzalkonium chloride (BAK), polymeric quaternary ammonium compound (PQAM), biguanides, sorbic acid, chlorhexidine or others. Of these, benzalkonium chloride and polymeric quaternary ammonium compound such as polyquaternium-1 have proven quite desirable.

The polymeric quaternary ammonium compounds useful in the compositions of the present invention are those which have an antimicrobial effect and which are ophthalmically acceptable. Preferred compounds of this type are described in U.S. Pat. Nos. 3,931,319; 4,027,020; 4,407,791; 4,525,346; 4,836,986; 5,037,647 and 5,300,287; and PCT application WO 91/09523 (Dziabo et al.). The most preferred polymeric ammonium compound is polyquaternium-1, otherwise known as POLYQUAD® with a number average molecular weight between 2,000 to 30,000. Preferably, the number average molecular weight is between 3,000 to 14,000.

When used, the polymeric quaternary ammonium compound is generally used in the composition of the present invention in an amount that is greater than about 0.00001 w/v %, more typically greater than about 0.0003 w/v % and even more typically greater than about 0.0007 w/v % of the ophthalmic composition. Moreover, the polymeric quaternary ammonium compound is generally used in the composition of the present invention in an amount that is less than about 0.01 w/v %, more typically less than about 0.007 w/v %, even more typically less than 0.003 w/v %, still more typically less than 0.0022 w/v % and even possibly less than about 0.0015 w/v % of the ophthalmic composition.

BAK is generally used in the composition of the present invention in an amount that is greater than about 0.001 w/v %, more typically greater than about 0.003 w/v % and even more typically greater than about 0.007 w/v % of the ophthalmic composition. Moreover, BAK is generally used in the composition of the present invention in an amount that is less than about 0.1 w/v %, more typically less than about 0.03 w/v % and even more typically less than about 0.020 or 0.015 w/v % of the ophthalmic composition.

It is also contemplated that the composition of the present invention may benefit from the use of two different polyols, borate and a preservative (e.g., BAK or polymeric quaternary ammonium compound) to provide enhanced preservations efficacy. Examples of such systems are disclosed in U.S. Patent Publication Nos. 2009/0232763 and 2010/0324031, which are expressly incorporated herein in their entirety for all purposes.

Notably, it has been found that polymeric ammonium compound is particularly desirable for preserving compositions containing SAE-β-CD while BAK is particularly desirable for preserving compositions containing hydroxypropyl beta or gamma cyclodextrin derivatives. It has also been found that filtration (e.g., micron filtration) of the preservative followed by aseptic addition of the preservative to the sterile composition can aid preservation efficacy.

It is contemplated that the composition of the present invention can include a variety of additional ingredients. Such ingredients include, without limitation, additional therapeutic agents, additional or alternative antimicrobial agents, suspension agents, surfactants, additional or alternative tonicity agents, additional or alternative buffering agents, anti-oxidants, additional or alternative viscosity-modifying agents, chelating agents any combinations thereof or the like.

The compositions of the present invention will generally be formulated as sterile aqueous solutions. The compositions of the present invention are also a) formulated so as to be compatible with the eye and/or other tissues to be treated with the compositions. The ophthalmic compositions intended for direct application to the eye will be formulated so as to have a pH and tonicity that are compatible with the eye. It is also contemplated that the compositions can be suspensions or other types of solutions.

The composition of the present invention will typically have a pH in the range of 4 to 9, preferably 5.5 to 8.5, and most preferably 5.5 to 8.0. Particularly desired pH ranges are 6.0 to 7.8 and more specifically 6.4 to 7.2. The compositions will have an osmolality of 200 to 400 or 450 milliosmoles per kilogram (mOsm/kg), more preferably 240 to 360 mOsm/kg.

It is generally preferred that the composition of the present invention be provided in an eye dropper that is configured to dispense the composition as eyedrops topically to the cornea of the eye. However, desired size of a single eyedrop (i.e., droplet size) for the ophthalmic composition can be difficult to accomplish. It has been discovered that the cyclodextrin in the composition imparts a relatively high surface energy to the composition. In turn, droplet size tends to be relatively high. It has been discovered, however, that by dispensing droplets through a relatively small orifice and/or by maintaining the viscosity of the composition within the ranges discussed above, desired droplet size can be achieved. Desired droplet size is typically at least 10 μl, more typically at least 18 μl and even more typically at least 23 μl, but is typically no greater than 60 μl, typically no greater than 45 μl and is typically no greater than 33 μl. Advantageously, this droplet size for the composition with the concentrations of olopatadine specified herein allows an individual to dispense one droplet per eye once a day and receive relief from symptoms of ocular allergic conjunctivitis generally, but particularly receive relief from late phase symptoms ocular allergic conjunctivitis.

In a preferred embodiment, the composition of the present invention is a multi-dose ophthalmic compositions that have sufficient antimicrobial activity to allow the compositions to satisfy the USP preservative efficacy requirements, as well as other preservative efficacy standards for aqueous pharmaceutical compositions.

The preservative efficacy standards for multi-dose ophthalmic solutions in the U.S. and other countries/regions are set forth in the following table:

Preservative Efficacy Test ("PET") Criteria (Log Order Reduction of Microbial Inoculum Over Time

|  | Bacteria | Fungi |
| --- | --- | --- |
| USP 27 | A reduction of 1 log (90%), by day 7; 3 logs (99.9%) by day 14; and no increase after day 14 | The compositions must demonstrate over the entire test period, which means no increases of 0.5 logs or greater, relative to the initial inoculum |
| Japan | 3 logs by 14 days; and no increase from day 14 through day 28 | No increase from initial count at 14 and 28 days |
| Ph. Eur. A[1] | A reduction of 2 logs (99%) by 6 hours; 3 logs by 24 hours; and no recovery after 28 days | A reduction of 2 logs (99%) by 7 days, and no increase thereafter |
| Ph. Eur. B | A reduction of 1 log at 24 hours; 3 logs by day 7; and no increase thereafter | A reduction of 1 log (90%) by day 14, and no increase thereafter |
| FDA/ISO 14730 | A reduction of 3 logs from initial challenge at day 14; and a reduction of 3 logs from rechallenge | No increase higher than the initial value at day 14, and no increase higher than the day 14 rechallenge count through day 28 |

[1]There are two preservative efficacy standards in the European Pharmacopoeia '"A" and "B".

The standards identified above for the USP 27 are substantially identical to the requirements set forth in prior editions of the USP, particularly USP 24, USP 25 and USP 26.

Advantages and Problems Overcome

The olopatadine ophthalmic composition of the present invention can provide multiple advantages over the olopatadine compositions that came before it. The composition disclosed herein provides an aqueous ophthalmic composition having a relatively high concentration of olopatadine that provides enhanced relief from late phase allergic conjunctivitis and early phase allergic conjuctivitis. Surprisingly and advantageously, preferred compositions of the present invention, as shown in FIGS. 1 through 5 and tables K through O, showed improved reduction in early phase redness, in late phase redness and in late phase itching. It is surprising that the enhanced concentration of olopatadine showed such significant reduction in late phase symptoms. It is even more surprising that the enhanced concentration of olopatadine showed enhanced reduction of early phase redness since it was generally believed that itching and redness would show similar responses to different concentrations of olopatadine.

Further, the composition can solubilize the relatively high concentration of olopatadine in solution form suitable as an eyedrop where other formulations have failed. Further yet, the composition can solubilize the higher concentrations of olopatadine while maintaining efficacy in treatment of the symptoms of allergic conjunctivitis where other efforts to develop such a solution have failed. Still further, the compositions can, when in multi-dose form, pass preservation efficacy standards where other compositions have failed.

As an additional advantage, it has been discovered that, for the particular composition of the present invention, composition containing HP-γ-CD have unexpectedly been found to be more susceptible to preservation. It has also unexpectedly been found to have solubility characteristics similar to the other beta cyclodextrin derivative discussed herein. This discovery has been particularly advantageous in providing a composition that is capable of solubilizing relatively high concentrations of olopatadine, capable of being stable for extended time periods and capable of robust preservation relative to both European and United States preservation efficacy standards.

It is still further advantageous that the cyclodextrin does not appear to interfere with the efficacy of the olopatadine. In particular, cyclodextrins have been found to entrap other drugs in a manner that does not allow those drugs to later release and show efficacy. However, this was not the case for olopatadine and was particularly not the case for HP-γ-CD.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

Table A below provides a listing of exemplary ingredients suitable for an exemplary preferred formulation of the ophthalmic composition of the present invention and a desired weight/volume percentage for those ingredients. It shall be understood that the following Table A is exemplary and that certain ingredients may be added or removed from the Table and concentrations of certain ingredients may be changed while the formulation can remain within the scope of the present invention, unless otherwise specifically stated.

TABLE A

| Ingredient | w/v percent |
|---|---|
| Olopatadine (Olopatadine HCl) | 0.7 |
| Polyether (PEG) | 4.0 |
| Lactam Polymer (PVP) | 4.0 |
| Viscosity Agent (HEC) | 0.1 (if used w/ HPMC or other viscosity agent) |
| | 0.3 (if used w/o HPMC or other viscosity agent) |
| Viscosity Agent (HPMC) | 0.15 (if used w/ HEC or other viscosity agent) |
| | 0.35 (if used w/o HEC or other viscosity agent) |
| Chelating agent (Disodium EDTA) | 0.005 |
| Borate (Boric Acid) | 0.3 |
| γ-cyclodextrin derivative and or β-cyclodextrin derivative | 1.0 for SAE-β-CD or 1.5 HP-β-CD or 1.5 HP-γ-CD |
| Polyol (Mannitol) | 0.3 |
| Polyol (Propylene Glycol) | 1.0 |
| Tonicity Agent (Sodium Chloride) | 0.35 |
| Preservative | 0.01 for BAK or 0.0015 PQAM |
| pH adjusting agents (NaOH or HCl) | sufficient to achieve pH = 7.0 |
| purified water | Q.S. 100 |

The following examples are presented to further illustrate selected embodiments of the present invention. The formulations shown in the examples were prepared using procedures that are well-known to persons of ordinary skill in the field of ophthalmic pharmaceutical compositions.

EXAMPLES

Preparatory Example 1

| Ingredients | Composition (w/w) |
|---|---|
| Olopatadine hydrochloride | 0.77 g |
| Hydroxypropyl-β-Cyclodextrin(HP-β-CD) | 1.5 g |
| PEG400(Polyethylene glycol 400) | 4.0 g |
| PVP(Polyvinylpyrrolidone K30) | 4.0 g |
| HPMC (Methocel E4m Premium) | 0.6 g |
| HEC(Natrosol 250HX) | 0.3 g |
| Disodium EDTA | 0.01 g |
| Mannitol | 0.6 g |
| Boric Acid | 0.3 g |
| Benzalkonium Chloride | 0.01 g |
| HCl/NaOH | q.s. to pH 7.0 |
| Purified water | q.s. to 100 g |

In a clean suitable and tared glass bottle, add and dissolve HPMC with an amount of purified water at 90-95° C. equivalent to about 15% of the required batch size. Mix by stirring until homogenization. Bring to the 35% of the final weight with purified water and mix by stirring with propeller until complete dispersion. Add HEC and mix by stirring until homogenization. Steam sterilize the solution (122° C./20 min) and cool afterwards (Part A). In a separate vessel with a stir bar, add an amount of purified water equivalent to about 40% of the required batch size. Add and dissolve batch quantities of weighed PEG400, PVP, HP-β-CD, Olopatadine HCl, Boric Acid, Mannitol, EDTA and BAC, allowing each component to dissolve before adding the next component. Check the pH and adjust to 7.0±0.1 with the required amount of NaOH 2N (Part B). In a laminar flow hood (sterile conditions), filter the solution Part B into the glass bottle containing the autoclaved fraction (Part A), using GV PVDF membrane, 0.22 μm filter unit and stir until homogenization. Mix by stirring with propeller for 15 min. Check the pH and adjust to 7.0±0.1 with the required amount of NaOH 1N/HCl 1N, if necessary. Bring to final weight with sterile purified water and stir until homogenization.

Preparatory Example 2

| Ingredients | Composition (w/w) |
|---|---|
| Olopatadine hydrochloride | 0.77 g |
| Hydroxypropyl-β-Cyclodextrin (HP-β-CD) | 1.5 g |
| PVP(Polyvinylpyrrolidone K30) | 4.0 g |
| PEG400(Polyethylene glycol 400) | 4.0 g |
| HPMC (Methocel E4m Premium) | 0.2 g |
| HEC(Natrosol 250HX) | 0.125 g |
| Disodium EDTA | 0.01 g |
| Boric Acid | 0.3 g |
| Benzalkonium Chloride | 0.01 or 0.015 g |
| NaOH 1N | 0.83 ml |
| HCl 1N | 0.58 ml |
| HCl/NaOH | q.s. to pH 7.0 |
| Purified water | q.s. to 100 g |

In a clean suitable and tared glass bottle, add and dissolve HPMC with an amount of purified water at 90-95° C. equivalent to about 15% of the required batch size. Mix by stirring until homogenization. Bring to the 30% of the final weight with purified water and mix by stirring with propeller until complete dispersion. Add HEC and mix by stirring until homogenization (Part A). In a clean beaker with stir bar, weigh an amount of purified water equivalent to about 40% of the required batch size. Heat and maintain this water around 70-75° C. Add NaOH 1N and mix by moderate stirring. Add PVP and dissolve under agitation during 20 minutes. Add HCl 1N, mix and quickly cool down to 30-40° C. Add and dissolve batch quantities of PEG400, HP-β-CD, Olopatadine HCl, Boric Acid, EDTA and BAC, allowing each component to dissolve before adding the next component. Check the pH of the solution and adjust to 6.8±0.1 with the required amount of NaOH 2N (Part B). Transfer Part B to Part A and stir the batch until it is homogenous. Bring to the 85% of the final weight with purified water and stir until homogenization. Steam sterilize the solution (122° C./20 min) and cool afterwards. In a laminar flow hood (sterile conditions), check the pH and adjust to 7.0±0.1 with the required amount of NaOH 1N/HCl 1N, if necessary. Bring to final weight with sterile purified water and stir until homogenization.

Formulary Examples A Through I in Table B Below

Formulary Examples A through I show the solubility of olopatadine in different formulations.

| Ingredients | A | B | C | D | E |
|---|---|---|---|---|---|
| PEG 400 | 4 | 4 | 4 | 4 | 3.8 |
| Dibasic Sodium Phosphate, anhydrous | 0.15 | — | — | — | 0.5 |
| Hydroxypropyl-β-Cyclodextrin | — | 1.5 | 1.5 | 1.5 | 1 |
| Sulfobutyl ether β Cyclodextrin | 2 | — | — | — | — |
| PVP K29/32 | 5 | 5 | 3 | 4 | 1.5 |
| Polysorbate 80 | 0.1 | — | — | — | — |
| Tyloxapol | — | — | — | — | — |
| Natrosol 250HX | 0.3 | 0.3 | 0.3 | 0.3 | — |
| HPMC 2910 | 0.6 | 0.6 | 0.6 | 0.6 | — |
| Boric Acid | — | 0.3 | 0.3 | 0.3 | — |
| Sodium Chloride | 0.15 | — | — | — | — |
| Mannitol | — | 0.6 | 0.6 | 0.6 | — |
| Benzalkonium Chloride | 0.01 | 0.01 | 0.01 | 0.01 | 0.01 |
| Disodium EDTA | 0.01 | 0.01 | 0.01 | 0.01 | 0.01 |
| Sodium Hydroxide/Hydrochloric Acid quantity sufficient to achieve pH of 7.4 | | | | | |
| Purified water quantity sufficient to 100% | | | | | |
| Olopatadine Solubility (%) | 1.064 | 0.901 | 0.725 | 0.811 | 0.461 |

| Ingredients | F | G | H | I |
|---|---|---|---|---|
| PEG 400 | 6 | 6 | 6 | 6 |
| Dibasic Sodium Phosphate, anhydrous | 0.5 | 0.5 | 0.5 | 0.5 |
| Hydroxypropyl-β-Cyclodextrin | — | 1 | 1 | 1 |
| Sulfobutyl ether β Cyclodextrin | — | — | — | — |
| PVP K29/32 | 1.5 | — | 1.5 | 1.5 |
| Polysorbate 80 | — | — | — | — |
| Tyloxapol | — | — | — | 0.05 |
| Natrosol 250HX | — | — | — | — |
| HPMC 2910 | — | — | — | — |
| Boric Acid | — | — | — | — |
| Sodium Chloride | — | — | — | — |
| Mannitol | — | — | — | — |
| Benzalkonium Chloride | 0.01 | 0.01 | 0.01 | 0.01 |
| Disodium EDTA | 0.01 | 0.01 | 0.01 | 0.01 |
| Sodium Hydroxide/Hydrochloric Acid quantity sufficient to achieve pH of 7.4 | | | | |
| Purified water quantity sufficient to 100% | | | | |
| Olopatadine Solubility (%) | 0.352 | 0.450 | 0.513 | 0.494 |

As can be seen, cyclodextrin can significantly enhance the solubility of olopatadine in aqueous solution. Moreover, it will be understood that the formulations of lower solubility, particularly those without cyclodextrin, will also typically exhibit worse solubility characteristics over time and tend to form precipitates.

Formulary Example J Through M in Table C Below

Formulary Examples J through M show the preservation efficacy of olopatadine containing formulations both with and without β-cyclodextrin.

| Ingredients | J | K | L | M |
|---|---|---|---|---|
| Olopatadine HCL | 0.77 | 0.77 | 0.77 | 0.77 |
| PEG 400 | — | 4 | — | — |
| Sodium Pyruvate | — | — | — | — |
| Dibasic Sodium Phosphate, anhydrous | 0.15 | 0.15 | 0.15 | 0.1 |
| Purified Guar | — | — | — | 0.17 |
| Hydroxypropyl-β-Cyclodextrin | 1.5 | — | — | 5 |
| PVP K30 | 2 | 3 | 3 | — |
| Tyloxapol | — | — | 0.2 | — |

-continued

| | | | | |
|---|---|---|---|---|
| Polysorbate 80 | — | 0.1 | — | — |
| Natrosol 250HX | — | 0.3 | 0.3 | — |
| HPMC 2910 | — | 0.6 | 0.6 | — |
| Boric Acid | — | — | — | 0.17 |
| Sodium Borate, decahydrate | — | — | — | 0.5 |
| Propylene Glycol | — | — | — | — |
| Sodium Chloride | — | 0.15 | 0.55 | 0.1 |
| Mannitol | 2.5 | — | — | — |
| Sorbitol | — | — | — | 1 |
| Sodium Citrate, dihydrate | — | — | — | 0.35 |
| Benzalkonium Chloride | 0.01 | 0.01 | 0.01 | 0.01 |
| Polyquaternium-1 | — | — | — | — |
| Disodium EDTA | 0.01 | 0.01 | 0.01 | — |
| Sodium Hydroxide/ Hydrochloric Acid | q.s. to pH 7.0 | q.s. to pH 7.0 | q.s. to pH 7.0 | q.s. to pH 7.0 |
| Purified water | q.s. to 100% | q.s. to 100% | q.s. to 100% | q.s. to 100% |

| PET | $Log_{10}$ Unit Reduction | | | |
|---|---|---|---|---|
| S. aureus | 0.1/1.9/ | 5.0/5.0/ | 1.5/5.0/ | 0.0/0.0/ |
| 6 h/24 h/7 d/14 d/28 d | 5.0/5.0/ 5.0 | 5.0/5.0/ 5.0 | 5.0/5.0/ 5.0 | 0.9/3.3/ 5.0 |
| P. aerugin | 4.9/4.9/ | 4.9/4.9/ | 4.9/4.9/ | 0.3/0.5/ |
| 6 h/24 h/7 d/14 d/28 d | 4.9/4.9/ 4.9 | 4.9/4.9/ 4.9 | 4.9/4.9/ 4.9 | 0.0/0.0/ 0.5 |
| E. coli | 2.8/4.9/ | 4.9/4.9/ | 4.9/4.9/ | 0.1/0.2/ |
| 6 h/24 h/7 d/14 d/28 d | 4.9/4.9/ 4.9 | 4.9/4.9/ 4.9 | 4.9/4.9/ 4.9 | 1.4/3.3/ 5.0 |
| C. albican | 4.3/5.1/ | 5.1/5.1/ | 2.5/5.1/ | 0.7/2.7/ |
| 7 d/14 d/28 d | 5.1/4.1/ 4.1 | 5.1/5.1/ 5.1 | 5.1 | 3.2 |
| A. niger | 0.8/0.9/ | 2.1/4.2/ | 0.7/1.7/ | 1.2/1.1/ |
| 7 d/14 d/28 d | 1.3 | 4.9 | 2.3 | 1.5 |

As can be seen, cyclodextrin derivatives can significantly inhibit the ability of a preservative to provide desired preservation to an aqueous formulation.

As an added advantage, it has also been discovered that HPMC can aid in solubilizing olopatadine. This effect is shown in Table D below.

TABLE D

| % PVP K29/32 | % SBE-CD | % PEG 400 | % HPMC | Concentration (mg/mL) | Final pH |
|---|---|---|---|---|---|
| 4 | 1.5 | 4 | — | 6.13 | 6.97 |
| 4 | 2.0 | 4 | — | 6.74 | 6.97 |
| 4 | 2.2 | 4 | — | 6.97 | 7.01 |
| 4 | 2.3 | 4 | — | 7.16 | 7.02 |
| 4 | 2.5 | 4 | — | 7.34 | 6.98 |
| 4 | 1.5 | 4 | 0.6 | 7.46 | 6.96 |
| 4 | 2.0 | 4 | 0.6 | 8.11 | 7.06 |
| 4 | 2.2 | 4 | 0.6 | 8.62 | 7.02 |
| 4 | 2.3 | 4 | 0.6 | 8.66 | 7.01 |
| 4 | 2.5 | 4 | 0.6 | 9.04 | 7.04 |

Table E below presents several formulations (N through Q) that can solubilize a high concentration of olopatadine using PVP in combination with a relatively low amount of HP-β-CD and that show desirable preservation using a combination of BAK and Boric Acid. Notably, PEG and HPMC are also believed to be aiding in the solubility of olopatadine.

TABLE E

| Ingredients | N | O | P | Q |
|---|---|---|---|---|
| Olopatadine HCL | 0.77 | 0.77 | 0.77 | 0.77 |
| PEG 400 | 4 | 4 | 4 | 4 |
| Hydroxypropyl-β-Cyclodextrin | 1.5 | 1.5 | 1.5 | 1.5 |
| PVP K29/32 | 4 | 4 | 4 | 4 |
| Natrosol 250HX | 0.3 | 0.3 | 0.3 | 0.125 |
| HPMC 2910 | 0.6 | 0.6 | 0.6 | 0.2 |
| Boric Acid | 0.3 | 0.3 | 0.3 | 0.3 |
| Disodium EDTA | 0.01 | 0.01 | 0.01 | 0.01 |
| Benzalkonium Chloride | 0.01 | 0.01 | 0.01 | 0.01 |
| Polyquaternium-1 | — | — | — | — |
| Sodium Hydroxide/ Hydrochloric Acid | q.s. to pH 7 | q.s. to pH 7 | q.s. to pH 7 | q.s. to pH 7 |
| Purified water | q.s. to 100% | q.s. to 100% | q.s. to 100% | q.s. to 100% |

| PET Result | $Log_{10}$ Unit Reduction | | | |
|---|---|---|---|---|
| S. aureus | 0.4/3.6/4.9/ | 0.2/1.4/5.0/ | 0.3/2.9/4.9/ | 0.4/3.2/5.0/5.0/ |
| 6 h/24 h/7 d/14 d/28 d | 4.9/4.9 | 5.0/5.0 | 4.9/4.9 | 5.0 |
| P. aerugin | 5.0/5.0/5.0/ | 5.1/5.1/5.1/ | 5.0/5.0/5.0/ | 5.2/5.2/5.2/5.2/ |
| 6 h/24 h/7 d/14 d/28 d | 5.0/5.0 | 5.1/5.1 | 5.0/5.0 | 5.2 |
| E. coli | 4.9/4.9/4.9/ | 2.7/5.1/5.1/ | 2.1/5.1/5.1/ | 2.3/5.1/5.1/5.1/ |
| 6 h/24 h/7 d/14 d/28 d | 4.9/4.9 | 5.1/5.1 | 5.1/5.1 | 5.1 |
| C. albican | 4.9/4.9/4.9 | 2.5/4.8/4.8 | 1.6/4.1/5.0 | 2.4/4.6/4.6 |
| 7 d/14 d/28 d | | | | |
| A. niger | 3.8/5.2/5.2 | 3.6/5.1/5.1 | 4.3/5.2/5.2 | 3.9/4.7/5.2 |
| 7 d/14 d/28 d | | | | |

Tables F and G below show the difficulty associated with preservation of formulations (R through X) containing SBE-β-CD.

TABLE F

| Ingredient | R | S | T | U |
|---|---|---|---|---|
| Olopatadine HCl | 0.77 | 0.77 | 0.77 | 0.77 |
| Sulfobutylether-β-Cyclodextrin | 0.75 | 0.75 | 0.75 | 0.75 |
| PVP K29/32 | 4 | 4 | 4 | 4 |
| PEG 400 | 2 | 2 | 2 | 2 |
| Natrosol 250HX | — | — | — | — |
| HPMC 2910 | 0.6 | 0.6 | 0.6 | 0.6 |
| Boric Acid | 0.6 | 0.3 | 0.3 | 0.3 |
| Mannitol | — | — | 0.2 | — |
| Disodium EDTA | — | 0.01 | 0.01 | 0.01 |
| Polyquaternium-1 | 0.001 | — | — | — |
| BAC | — | 0.02 | 0.02 | — |
| Benzododecinium Bromide | — | — | — | — |
| Sorbic Acid | — | — | — | 0.2 |
| Thimerosal | — | — | — | — |
| Chlorhexidine Digluconate | — | — | — | — |
| NaOH/HCl | q.s. to pH 7.0 | q.s. to pH 7.0 | q.s. to pH 7.0 | q.s. to pH 6.0 |
| Purified water | q.s. to 100 | q.s. to 100 | q.s. to 100 | q.s. to 100 |
| PET RESULTS | | | | |
| S. aureus 6 h/24 h/7 d/14 d/28 d | 1.8/2.8/5.0/5.4/ | 0.0/0.5/4.7/ | 0.0/0.4/4.7/ | 0.1/0.1/4.7/ |
| P. aerugin 6 h/24 h/7 d/14 d/28 d | 0.6/0.8/5.4/5.4/ | 5.0/5.0/5.0/ | 5.0/5.0/5.0/ | 5.0/5.0/5.0/ |
| E. coli 6 h/24 h/7 d/14 d/28 d | 1.2/3.2/5.4/5.4/ | 1.4/3.1/5.1/ | 1.7/3.2/5.1/ | 0.2/0.3/5.1/ |
| C. albicans 7 d/14 d/28 d | 0.3/1.5/ | 0.7/ | 0.6 | 0.1/ |
| A. Niger 7 d/14 d/28 d | 0.7/0.7/ | 2.1/ | 1.2 | 1.1/ |

TABLE G

| Ingredients | V | W | X |
|---|---|---|---|
| Olopatadine HCl | 0.77 | 0.77 | 0.77 |
| Sulfobutylether-β-Cyclodextrin | 0.75 | 0.75 | 0.75 |
| PVP K29/32 | 4 | 4 | 4 |
| PEG 400 | 2 | 2 | 2 |
| Natrosol 250HX | — | — | — |
| HPMC 2910 | 0.6 | 0.6 | 0.6 |
| Boric Acid | 0.3 | 0.3 | 0.3 |
| Mannitol | — | — | — |
| Disodium EDTA | 0.01 | 0.01 | 0.01 |
| Polyquaternium-1 | — | — | — |
| BAC | — | — | — |
| Benzododecinium Bromide | 0.02 | — | — |
| Sorbic Acid | — | — | — |
| Thimerosal | — | 0.01 | — |
| Chlorhexidine Digluconate | — | — | 0.01 |
| NaOH/HCl | q.s. to pH 7.0 | q.s. to pH 7.0 | q.s. to pH 7.0 |
| Purified water | q.s. to 100 | q.s. to 100 | q.s. to 100 |
| PET RESULTS | | | |
| S. aureus 6 h/24 h/7 d/14 d/28 d | 0.0/0.1/4.7/ | 0.0/0.0/4.7/ | 0.0/0.4/4.7/ |
| P. aerugin 6 h/24 h/7 d/14 d/28 d | 5.0/5.0/5.0/ | 5.0/5.0/5.0/ | 5.0/5.0/5.0/ |
| E. coli 6 h/24 h/7 d/14 d/28 d | 0.6/1.3/5.1/ | 1.1/5.0/5.0/ | 1.0/3.9/5.0/ |
| C. albicans 7 d/14 d/28 d | 0.5/ | 5.8/ | 3.9/ |
| A. Niger 7 d/14 d/28 d | 1.2/ | 5.0/ | 1.4 |

Tables H and I show the achievement of significantly improved preservation of formulations (Y through II), which also contain SBE-β-CD.

TABLE H

| Ingredients | Y | Z | AA | BB | CC | DD |
|---|---|---|---|---|---|---|
| | | | +++ | ++− | +−+ | −+− |
| Olopatadine HCl | 0.77 | 0.77 | 0.77 | 0.77 | 0.77 | 0.77 |
| Sulfobutylether-β-Cyclodextrin | 1.5 | 1.5 | 1 | 1 | 1 | 0.75 |
| PVP K29/32 | 4 | 4 | 4 | 4 | 4 | 4 |
| PEG 400 | 4 | 4 | 2 | 2 | 2 | 2 |
| Natrosol 250HX | 0.3 | 0.3 | — | — | — | — |
| HPMC 2910 | 0.6 | 0.6 | 0.6 | 0.6 | 0.6 | 0.6 |
| Boric Acid | 0.3 | 0.3 | 0.3 | 0.3 | 0.3 | 0.3 |

TABLE H-continued

| Ingredients | Y | Z | AA | BB | CC | DD |
|---|---|---|---|---|---|---|
| Mannitol | 0.6 | — | — | — | — | — |
| Propylene glycol | — | 1 | 1 | 0.5 | 1 | 0.5 |
| Polyquaternium-1 | 0.001 | 0.001 | 0.002 | 0.002 | 0.001 | 0.002 |
| Sodium Hydroxide and/or Hydrochloric acid Qs to pH 7.2 | | | | | | |
| Purified Water Qs to 100 | | | | | | |
| PET DATA | | | | | | |
| S. aureus 6 h/24h/7 d/ 14 d/28 d | 0.9/1.7/4.9/ 4.9/4.9 | 1.2/1.6/4.9/ 4.9/4.9 | 1.6/2.2/4.7/ 4.7/4.7 | 1.6/2.4/4.7/ 4.7/4.7 | 1.8/2.0/4.7/ 4.7/4.7 | 2.1/2.9/5.05 .0/ |
| P. aerugin 6 h/24 h/7 d/ 14 d/28 d | 3.4/4.9/4.9/ 4.9/4.9 | 0.3/1.4/5.2/ 5.2/5.2 | 0.0/1.0/4.6/ 5.1/5.1 | 0.2/1.2/5.1/ 5.1/5.1 | 0.1/1.0/5.1/ 5.1/5.1 | 0.6/1.5/5.45 .4/ |
| E. coli 6 h/24 h/7 d/ 14 d/28 d | 1.9/4.2/4.9/ 4.9/4.9 | 1.0/2.7/5.2/ 5.2/5.2 | 0.3/1.6/4.8/ 4.8/4.8 | 1.7/4.8/4.8/ 4.8/4.8 | 0.3/1.2/4.8/ 4.8/4.8 | 2.2/4.9/5.45 .4/ |
| C. albican 7 d/14 d/28 d | 0.1/0.4/0.4 | 0.9/1.1/2.1 | 1.2/2.5/ | 1.0/2.2/ | 0.8/2.3/ | 0.9/2.7/ |
| A. niger 7 d/14 d/28 d | 3.6/3.6/3.1 | 1.0/1.0/1.0 | 0.6/0.7/ | 0.2/0.8/ | 0.2/0.8/ | 0.6/0.8/ |

TABLE I

| FID | EE | FF | GG | HH | II |
|---|---|---|---|---|---|
|  | -++ | --- | +-- | --+ | NA |
| Olopatadine HCl | 0.77 | 0.77 | 0.77 | 0.77 | 0.77 |
| Sulfobutylether-β-Cyclodextrin | 0.75 | 0.75 | 1 | 0.75 | 0.75 |
| PVP K29/32 | 4 | 4 | 4 | 4 | 4 |
| PEG 400 | 2 | 2 | 2 | 2 | 2 |
| Natrosol 250HX | — | — | — | — | — |
| HPMC 2910 | 0.6 | 0.6 | 0.6 | 0.6 | 0.6 |
| Boric Acid | 0.3 | 0.3 | 0.3 | 0.3 | 0.6 |
| Mannitol | — | — | — | — | — |
| Propylene glycol | 1 | 0.5 | 0.5 | 1 | — |
| Polyquaternium-1 | 0.002 | 0.001 | 0.001 | 0.001 | 0.001 |
| Sodium Hydroxide and/or Hydrochloric acid Qs to pH 7.2 | | | | | |
| Purified Water Qs to 100 | | | | | |
| PET DATA | | | | | |
| S. aureus 6 h/24 h/7 d/ 14 d/28 d | 2.0/3.1/4.7/ 4.7/4.7 | 0.7/1.2/4.7/ 4.7/4.7 | 1.5/1.8/4.7/ 4.7/4.7 | 2.0/2.9/5.05.0/ | 1.8/2.8/5.05.4/ |
| P. aerugin 6 h/24 h/7 d/ 14 d/28 d | 0.5/1.4/5.1/ 5.1/5.1 | 0.0/0.4/2.0/ 1.2/0.2 | 0.4/1.1/5.1/ 5.1/5.1 | 0.6/6.3/5.45.4/ | 0.6/0.8/5.45.4/ |
| E. coli 6 h/24 h/7 d/ 14 d/28 d | 1.6/4.6/4.8/ 4.8/4.8 | 0.0/0.0/0.00 .0/2.6 | 0.2/0.8/4.8/ 4.8/4.8 | 2.4/5.2/5.45.4/ | 1.2/3.2/5.45.4/ |
| C. albican 7 d/14 d/28 d | 1.1/2.7/ | 0.6/1.9/ | 0.7/1.9/ | 0.3/2.4/ | 0.3/1.5/ |
| A. niger 7 d/14 d/28 d | 0.7/0.8/ | 0.7/0.9/ | 0.7/0.8/ | 0.7/0.8/ | 0.7/0.7/ |

Table J illustrates that formula preservation can best be achieved using HP-γ-CD. In particular, formulas JJ through TT in Table J exhibit robust preservation relative to both European and United States preservation standards. This is particularly surprising when the data in Table J is compared with the data in Tables A, B and E since there is no readily identifiable reason that the formulations containing HP-γ-CD should exhibit greater preservation efficacy relative to the formulations containing HP-β-CD.

TABLE J

| Formula | JJ | KK | LL | MM | NN | OO |
|---|---|---|---|---|---|---|
| Batch # | 11-63920 | 11-63921 | 11-63900 | 11-63901 | 11-63902 | 11-63922 |
| Component | | | | | | |
| Olopatadine Hydrochloride | 0.77 | 0.77 | 0.77 | 0.77 | 0.77 | 0.77 |
| HP-γ-CD | 1.5 | 1.5 | 1.5 | 1.5 | 1.5 | 1.5 |
| Povidone K29/32 | 4 | 4 | 4 | 4 | 4 | 4 |

TABLE J-continued

| | | | | | | |
|---|---|---|---|---|---|---|
| PEG 400 | 4 | 4 | 4 | 4 | 4 | 4 |
| HPMC 2910 E4M | 0.4 | 0.4 | 0.4 | 0.4 | 0.4 | 0.4 |
| Boric acid | 0.3 | 0.3 | 0.3 | 0.3 | 0.3 | 0.3 |
| Mannitol | 0.2 | 0.2 | 0.2 | 0.2 | 0.2 | 0.2 |
| Disodium EDTA | — | — | — | — | — | 0.005 |
| Benzalkonium Chloride | 0.015 | 0.0125 | 0.01 | 0.0075 | 0.005 | 0.015 |

Sodium Hydroxide and/or Hydrochloric acid Qs to pH 7.2
Purified Water Qs to 100

PET DATA

| | | | | | | |
|---|---|---|---|---|---|---|
| S. aureus 6 h/24 h/7 d/14 d/28 d | 4.9/4.9/4.9/ 4.9/4.9 | 4.9/4.9/4.9/ 4.9/4.9 | 4.8/4.8/4.8/ 4.8/4.8 | 4.8/4.8/4.8/ 4.8/4.8 | 4.8/4.8/4.8/ 4.8/4.8 | 4.9/4.9/4.9/ 4.9/4.9 |
| P. aeruginosa 6 h/24 h/7 d/14 d/28 d | 4.9/4.9/4.9/ 4.9/4.9 | 4.9/4.9/4.9/ 4.9/4.9 | 4.9/4.8/4.9/ 4.9/4.9 | 4.9/4.9/4.9/ 4.9/4.9 | 4.9/4.9/4.9/ 4.9/4.9 | 4.9/4.9/4.9/ 4.9/4.9 |
| E. coli 6 h/24 h/7 d/14 d/28 d | 5.0/5.0/5.0/ 5.0/5.0 | 2.6/5.0/5.0/ 5.0/5.0 | 1.1/3.0/4.9/ 4.9/4.9 | 0.9/1.8/4.9/ 4.9/4.9 | 0.4/1.2/4.9/ 4.9/4.9 | 5.0/5.0/5.0/ 5.0/5.0 |
| C. albican 6 h/24 h/7 d/14 d/28 d | 4.8/4.8/4.8 | 4.8/4.8/4.8 | 4.9/4.9/4.9 | 4.9/4.9/4.9 | 4.9/4.9/4.9 | 4.8/4.8/4.8 |
| A. niger 6 h/24 h/7 d/14 d/28 d | 5.1/5.1/5.1 | 5.1/5.1/5.1 | 5.1/5.1/5.1 | 5.1/5.1/5.1 | 5.1/5.1/5.1 | 5.1/5.1/5.1 |
| Test Results pH Initial | 7.31 | 7.25 | 7.25 | 7.20 | 7.29 | 7.25 |

| FID | PP | QQ | RR | SS | TT |
|---|---|---|---|---|---|
| Batch # | 11-63923 | 11-63899 | 11-63905 | 11-63908 | 11-64011 |
| Component | | | | | |
| Olopatadine Hydrochloride | 0.77 | 0.77 | 0.77 | 0.77 | 0.77 |
| HP-γ-CD | 1.5 | 1.5 | 1.5 | 1.5 | 1.5 |
| Povidone K29/32 | 4 | 4 | 4 | 4 | 4 |
| PEG 400 | 4 | 4 | 4 | 4 | 4 |
| HPMC 2910 E4M | 0.4 | 0.4 | 0.4 | 0.4 | 0.4 |
| Boric acid | 0.3 | 0.3 | 0.3 | 0.3 | 0.3 |
| Mannitol | 0.2 | 0.2 | 0.2 | 0.2 | 0.2 |
| Disodium EDTA | 0.005 | 0.005 | 0.005 | 0.005 | 0.005 |
| Benzalkonium Chloride | 0.0125 | 0.01 | 0.0075 | 0.005 | 0.01 |

Sodium Hydroxide and/or Hydrochloric acid Qs to pH 7.2
Purified Water Qs to 100

PET DATA

| | | | | | |
|---|---|---|---|---|---|
| S. aureus 6 h/24 h/7 d/14 d/28 d | 4.9/4.9/4.9/ 4.9/4.9 | 4.8/4.8/4.8/ 4.8/4.8 | 4.8/4.8/4.8/ 4.8/4.8 | 4.9/4.9/4.9/ 4.9/4.9 | 5.0/5.0/5.0/ 5.0/5.0 |
| P. aeruginosa 6 h/24 h/7 d/14 d/28 d | 4.9/4.9/4.9/ 4.9/4 .9 | 4.9/4.9/4.9/ 4.9/4.9 | 4.9/4.9/4.9/ 4.9/4.9 | 4.9/4.9/4.9/ 4.9/4.9 | 5.0/5.0/5.0/ 5.0/5.0 |
| E. coli 6 h/24 h/7 d/14 d/28 d | 5.0/5.0/5.0/ 5.0/5.0 | 4.9/4.9/4.9/ 4.9/4.9 | 4.9/4.9/4.9/ 4.9/4.9 | 5.0/5.0/5.0/ 5.0/5.0 | 5.1/5.1 /5.1/ 5.1/5.1 |
| C. albican 6 h/24 h/7 d/14 d/28 d | 4.8/4.8/4.8 | 4.9/4.9/4.9 | 4.9/4.9/4.9 | 4.8/4.8/4.8 | 4.9/4.9/4.9 |
| A. niger 6 h/24 h/7 d/14 d/28 d | 4.4/5.1/5.1 | 5.1/5.1/4.9 | 5.1/5.1/5.1 | 4.4/5.1/5.1 | 5.3/5.3/5.3 |
| Test Results pH Initial | 7.24 | 7.24 | 7.23 | 7.28 | 7.29 |

Tables K through O below corresponding to graphs in FIGS. 1 through 5, provide results from a conjunctival allergen challenge (CAC) study of a high concentration olopatadine composition as compared to a marketed lower concentration olopatadine composition (marketed as PATADAY® by Alcon Laboratories, Inc., a Novartis Company). The CAC study was performed according to a standard CAC model that instills allergen in the eye (the challenge) and then makes determinations of ocular redness and ocular itching at time points (determination times) after the challenge. The CAC study was performed by ORA, Inc., Andover, Mass., United States, 01810, which uses a model accepted by the food and drug administration (FDA). It is noted that in tables K through O and FIGS. 1 through 5, the references to 0.77% olopatadine are references to olopatadine HCL and actually represent 0.7% olopatadine as base and the references to 0.2% olopatadine are references to 0.22% olopatadine HCL and 0.2% olopatadine as base.

In the CAC model, each patient is dosed with drug or vehicle and exposed to allergen at specific challenge times. The challenge times for the study were 27 minutes, 16 hours and 24 hours after dosing. Thereafter, itching is determined at determination times of 3, 5 and 7 minutes after challenge times and redness is determined at determination times of 7, 15 and 20 minutes after the challenge times. Therefore, patients received three doses of drug or vehicle and each dose was followed by an allergen challenge and then the itching and redness determination are made as discussed. Results from the determination times are provided in Tables K through O and the graphs of FIGS. 1 through 5.

Redness scores are determined on a scale of 0 to 4 by visual observation and the patient is asked to rate their ocular itching on a scale of 0 to 4 to attain itching scores and in each score 0 is the least and 4 is greatest. The results of those determinations at those time points are provided in Tables K through O and the graphs of FIGS. 1 through 5. Each of Tables K through O provide a mean score (Mean), a standard deviation (Std) to that score, a number (N) of patients, a minimum (Min) score determined for any of the patients, a maximum (Max) score determined for any of the patients and p-values for indications of statistical significance with a p-value of less than 0.05 indicating statistical significance.

Table K below provides data relative to mean conjunctival redness as determined by the conjunctival allergen challenge (CAC) study 27 minutes after challenge and that data is provided as a graph in FIG. 1.

TABLE K

| | | Conjunctival Redness (Onset-of-Action CAC) | | | | | By Time | Overall |
|---|---|---|---|---|---|---|---|---|
| | | Mean | Std | N | Min | Max | p-value | p-value |
| 7 min | Olopatadine 0.77% | 0.8 | 0.7 | 63 | 0 | 3 | | |
| | Olopatadine 0.2% | 1.3 | 0.8 | 63 | 0 | 3 | <.0001 | <.0001 |
| | Vehicle | 2.1 | 0.7 | 60 | 0 | 3 | <.0001 | <.0001 |
| 15 min | Olopatadine 0.77% | 1.1 | 0.9 | 63 | 0 | 3 | | |
| | Olopatadine 0.2% | 1.9 | 0.8 | 63 | 0 | 3 | <.0001 | |
| | Vehicle | 2.3 | 0.6 | 60 | 1 | 4 | <.0001 | |
| 20 min | Olopatadine 0.77% | 1.1 | 0.8 | 63 | 0 | 3 | | |
| | Olopatadine 0.2% | 1.9 | 0.8 | 63 | 0 | 3 | <.0001 | |
| | Vehicle | 2.3 | 0.7 | 60 | 0 | 4 | <.0001 | |

Main Effect of Treatment p-value = <.0001
Treatment by Time Interaction p-value = 0.0036

As can be seen in Table K and FIG. 1, olopatadine at a concentration of 0.7% (note that the 0.77% above is for olopatadine HCl and represents 0.7% olopatadine) provides statistically significant (i.e., p<0.05) relief of redness at onset-of-action relative to both vehicle and olopatadine 0.2%. Further, olopatadine at a concentration of 0.7% provides more that a 1.0 unit difference relative to vehicle in relief of redness. Olopatadine at this concentration is believed to be the first antihistamine/mast cell stabilizer to provide such a difference. This data is particularly surprising since, prior to this CAC study, there was no indication that a high concentrations olopatadine composition would provide any additional reduction in redness at onset-of-action.

Olopatadine's $IC_{50}$ value or half maximal inhibitory concentration ($IC_{50}$) for inhibition of human conjunctival mast cell degranulation is in the 500 to 600 µM range. Olopatadine's binding affinity (Ki) value for histamine binding to the H1 receptor is in the 30 to 50 nM range. The molar concentration of olopatadine in a 0.1% solution of olopatadine is approximately 2.5 mM. These values suggest that a 0.1% solution of olopatadine should have more than a sufficient quantity of olopatadine to provide maximal inhibition of human conjunctival mast cell degranulation and maximal fully histamine binding.

In particular, for inhibition of mast cell degranulation, these values indicate that when a 0.1% solution of olopatadine is dosed onto the eye, there is exposure to 5 times the $IC_{50}$ value for mast cell degranulation (500 µM vs 2.5 mM). When a 0.2% olopatadine solution is dosed to the eye, the exposure increases from approximately 2.5 mM (for a 0.1% solution) to 5 mM or about 10 times excess drug for inhibition of mast cell degranulation. Because olopatadine does not have any vasoconstrictive effect, which would typically reduce redness, this inhibition of redness is believed to result from inhibition of the release of the mast cell mediators brought about by the mast cell degranulation. As such, a 0.1% or 0.2% solution of olopatadine should provide full inhibition of redness at onset of action since both of these solutions provide excess olopatadine for inhibiting mast cell degranulation.

Surprisingly, however, the data in Table K and FIG. 1 show that a 0.7% solution of olopatadine prevents redness even better than a 0.2% solution of olopatadine at onset of action. Even more surprising, it provides a statistically significant difference in redness inhibition relative the 0.2% solution at onset of action.

In contrast to this surprising discovery relative to redness, a similar finding was not made for itching (see Table KK below), which is believed to be avoided through histamine binding.

TABLE KK

| | | Ocular Itching (Onset-of-Action CAC) | | | | | By Time | Overall |
|---|---|---|---|---|---|---|---|---|
| | | Mean | Std | N | Min | Max | p-value | p-value |
| 3 min | Olopatadine 0.77% | 0.4 | 0.7 | 63 | 0 | 3 | | |
| | Olopatadine 0.2% | 0.4 | 0.6 | 63 | 0 | 3 | 0.8434 | |
| | Vehicle | 1.9 | 1.1 | 60 | 0 | 4 | <.0001 | |
| 5 min | Olopatadine 0.77% | 0.6 | 0.8 | 63 | 0 | 3 | | |
| | Olopatadine 0.2% | 0.7 | 0.7 | 63 | 0 | 3 | 0.5341 | |
| | Vehicle | 2.1 | 1.1 | 60 | 0 | 4 | <.0001 | |
| 7 min | Olopatadine 0.77% | 0.5 | 0.7 | 63 | 0 | 3 | | |
| | Olopatadine 0.2% | 0.7 | 0.8 | 63 | 0 | 4 | 0.3667 | 0.5441 |
| | Vehicle | 2.0 | 1.1 | 60 | 0 | 4 | <.0001 | <.0001 |

Main Effect of Treatment p-value = <.0001
Treatment by Time Interaction p-value = 0.4025

The similarity in itching values for olopatadine 0.7% and olopatadine 0.2% for itching at onset of action are to be expected since 0.2% olopatadine and 0.7% olopatadine both provide enough olopatadine to provide maximal inhibition of itching at onset of action. Thus, the above discussed finding relative to redness at onset of action is quite unique.

Table L below provides data relative to mean conjunctival redness determined by the CAC study 16 hours after challenge and that data is provided as a graph in FIG. 2.

TABLE L

| | | Conjunctival Redness (16 hrs Duration CAC) | | | | | By Time | Overall |
|---|---|---|---|---|---|---|---|---|
| | | Mean | Std | N | Min | Max | p-value | p-value |
| 7 min | Olopatadine 0.77% | 1.3 | 0.8 | 65 | 0 | 3 | | |
| | Olopatadine 0.2% | 1.6 | 0.7 | 65 | 1 | 3 | 0.0123 | 0.0056 |
| | Vehicle | 1.8 | 0.8 | 65 | 1 | 3 | <.0001 | 0.0001 |
| 15 min | Olopatadine 0.77% | 1.5 | 0.8 | 65 | 0 | 4 | | |
| | Olopatadine 0.2% | 1.9 | 0.7 | 65 | 1 | 4 | 0.0061 | |
| | Vehicle | 1.9 | 0.8 | 65 | 1 | 4 | 0.0013 | |
| 20 min | Olopatadine 0.77% | 1.5 | 0.8 | 65 | 0 | 4 | | |
| | Olopatadine 0.2% | 1.9 | 0.7 | 65 | 1 | 4 | 0.0061 | |
| | Vehicle | 1.9 | 0.9 | 65 | 1 | 4 | 0.0015 | |

Main Effect of Treatment p-value = 0.0004
Treatment by Time Interaction p-value = 0.0077

Figure 2:
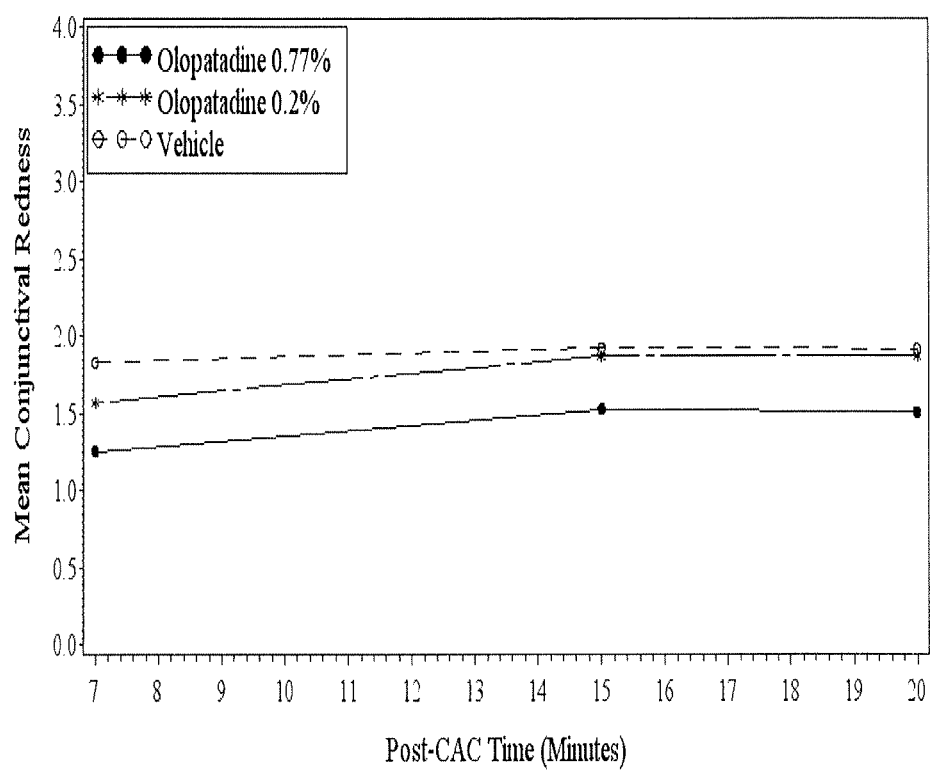
FIG. 2 is a graph of mean conjunctival redness determined by a conjunctival allergen challenge (CAC) at 16 hours.

As can be seen in Table L and FIG. 2, olopatadine at a concentration of 0.7% provides statistically significant relief of redness at 16 hours relative to both vehicle and olopatadine 2%.

Table M below provides data relative to mean total redness determined by the CAC study 24 hours after challenge and that data is provided as a graph in FIG. 3. Mean total redness is a summation three redness determinations: i) conjunctival; ii) episcleral; and iii) ciliary, each taken on a scale of 1 through 4.

TABLE M

|  |  | Total Redness (24 hrs Duration CAC) |  |  |  |  | By Time | Overall |
|---|---|---|---|---|---|---|---|---|
|  |  | Mean | Std | N | Min | Max | p-value | p-value |
| 7 min | Olopatadine 0.77% | 4.1 | 2.6 | 66 | 0 | 10 |  |  |
|  | Olopatadine 0.2% | 5.4 | 2.4 | 66 | 1 | 11 | 0.0022 | 0.0073 |
|  | Vehicle | 6.1 | 2.3 | 68 | 1 | 10 | <.0001 | <.0001 |
| 15 min | Olopatadine 0.77% | 5.0 | 2.9 | 66 | 0 | 10 |  |  |
|  | Olopatadine 0.2% | 6.2 | 2.3 | 66 | 1 | 11 | 0.0086 |  |
|  | Vehicle | 6.7 | 2.3 | 68 | 1 | 11 | <.0001 |  |
| 20 min | Olopatadine 0.77% | 5.4 | 2.9 | 66 | 1 | 11 |  |  |
|  | Olopatadine 0.2% | 6.3 | 2.3 | 66 | 2 | 11 | 0.0383 |  |
|  | Vehicle | 6.6 | 2.6 | 68 | 1 | 11 | 0.0040 |  |

Main Effect of Treatment p-value = 0.0003
Treatment by Time Interaction p-value = 0.0136

Figure 3:
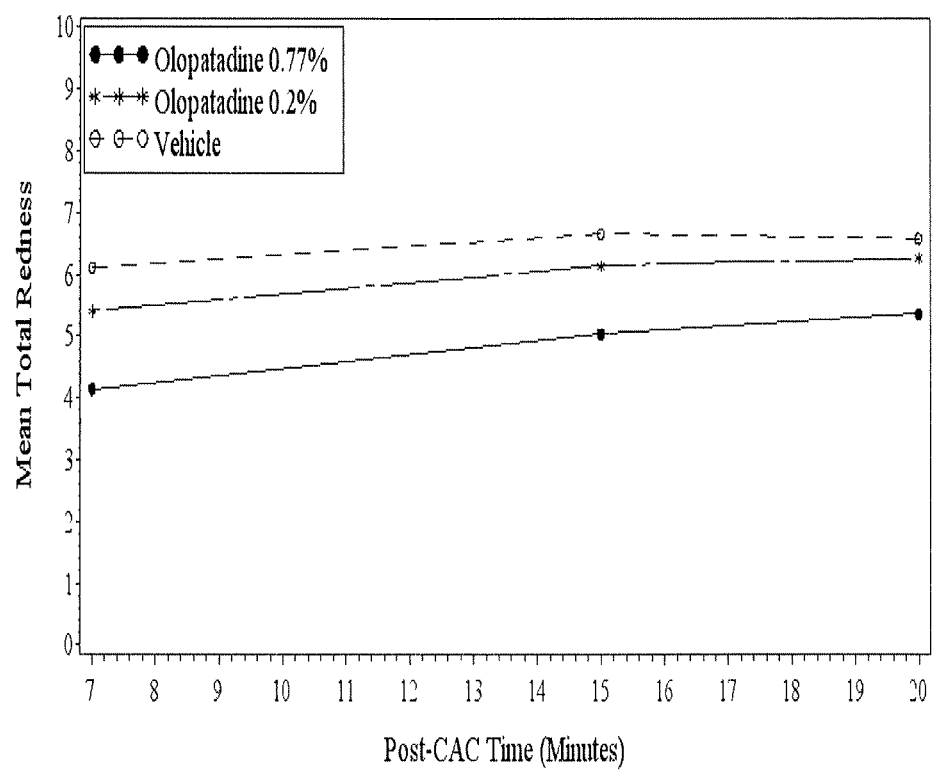
FIG. 3 is a graph of mean total redness determined by a conjunctival allergen challenge (CAC) at 24 hours.

As can be seen in Table M and FIG. 3, olopatadine at a concentration of 0.7% provides statistically significant relief of total redness at 24 hours relative to both vehicle and olopatadine 2%.

Table N below provides data relative to ocular itching determined by the CAC study 24 hours after challenge and that data is provided as a graph in FIG. 4.

TABLE N

|  |  | Ocular Itching (24 hrs Duration CAC) |  |  |  |  | By Time | Overall |
|---|---|---|---|---|---|---|---|---|
|  |  | Mean | Std | N | Min | Max | p-value | p-value |
| 3 min | Olopatadine 0.77% | 0.9 | 0.8 | 66 | 0 | 3 |  |  |
|  | Olopatadine 0.2% | 1.4 | 0.8 | 66 | 0 | 3 | 0.0010 |  |
|  | Vehicle | 2.5 | 0.8 | 68 | 1 | 4 | <.0001 |  |
| 5 min | Olopatadine 0.77% | 1.1 | 0.9 | 66 | 0 | 3 |  |  |
|  | Olopatadine 0.2% | 1.5 | 0.9 | 66 | 0 | 4 | 0.0107 |  |
|  | Vehicle | 2.6 | 0.8 | 68 | 0 | 4 | <.0001 |  |
| 7 min | Olopatadine 0.77% | 1.1 | 0.9 | 66 | 0 | 3 |  |  |
|  | Olopatadine 0.2% | 1.5 | 1.0 | 66 | 0 | 4 | 0.0149 | 0.0034 |
|  | Vehicle | 2.5 | 0.9 | 68 | 0 | 4 | <.0001 | <.0001 |

Main Effect of Treatment p-value = <.0001
Treatment by Time Interaction p-value = 0.3221

Figure 4:
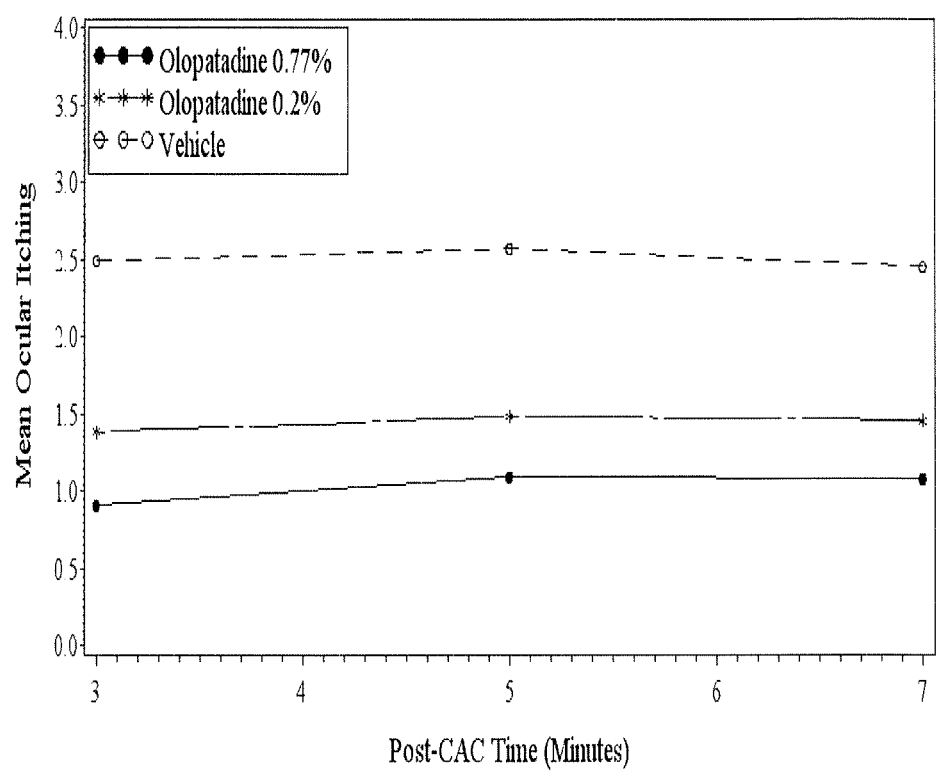
FIG. 4 is a graph of mean ocular itching determined by a conjunctival allergen challenge (CAC) at 24 hours.

As can be seen in Table N and FIG. 4, olopatadine at a concentration of 0.7% provides statistically significant relief of ocular itching at 24 hours relative to both vehicle and olopatadine 2%.

Table O below provides data relative to ocular itching determined by the CAC study 24 hours after challenge and that data is provided as a graph in FIG. 5.

TABLE O

|  |  | Conjunctival Redness (24 hrs Duration CAC) |  |  |  |  | By Time | Overall |
|---|---|---|---|---|---|---|---|---|
|  |  | Mean | Std | N | Min | Max | p-value | p-value |
| 7 min | Olopatadine 0.77% | 1.5 | 0.8 | 66 | 0 | 3 |  |  |
|  | Olopatadine 0.2% | 1.9 | 0.8 | 66 | 0 | 4 | 0.0016 | 0.0075 |
|  | Vehicle | 2.1 | 0.8 | 68 | 1 | 4 | <.0001 | <.0001 |
| 15 min | Olopatadine 0.77% | 1.8 | 0.9 | 66 | 0 | 4 |  |  |
|  | Olopatadine 0.2% | 2.1 | 0.7 | 66 | 0 | 4 | 0.0131 |  |
|  | Vehicle | 2.3 | 0.7 | 68 | 1 | 4 | <.0001 |  |
| 20 min | Olopatadine 0.77% | 1.8 | 0.9 | 66 | 0 | 4 |  |  |
|  | Olopatadine 0.2% | 2.1 | 0.7 | 66 | 1 | 4 | 0.0402 |  |
|  | Vehicle | 2.3 | 0.9 | 68 | 1 | 4 | 0.0024 |  |

Main Effect of Treatment p-value = 0.0002
Treatment by Time Interaction p-value = 0.1540

Figure 5:
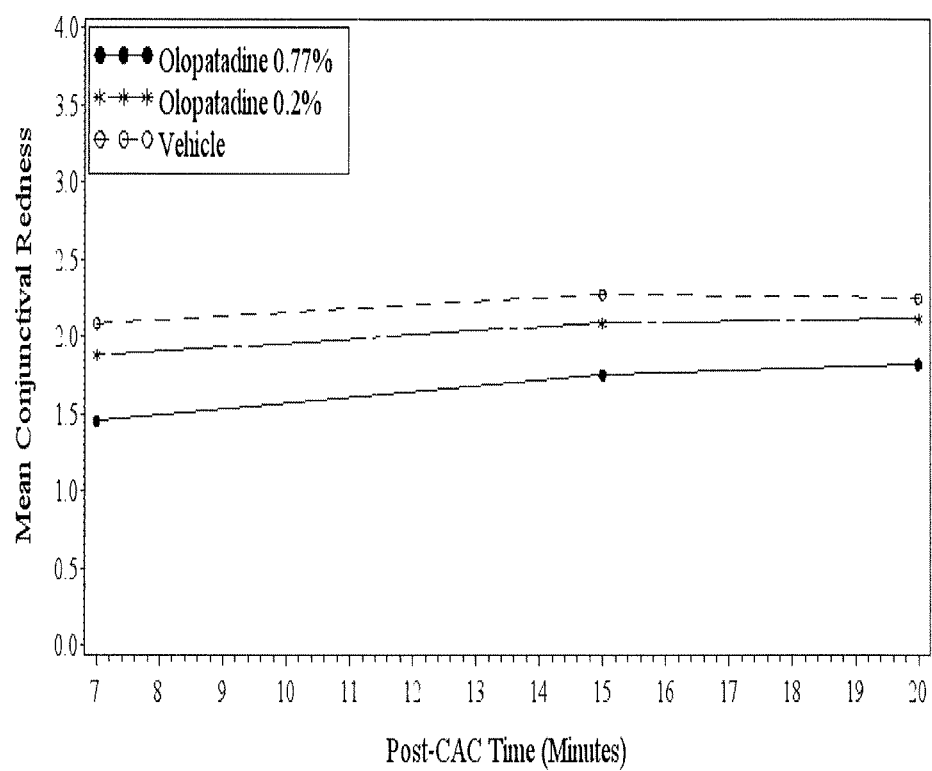
FIG. 5 is a graph of mean conjunctival redness determine by a conjunctival allergen challenge (CAC) at 24 hours.

As can be seen in Table O and FIG. 5, olopatadine at a concentration of 0.7% provides statistically significant relief of conjunctival redness at 24 hours relative to both vehicle and olopatadine 2%.

We claim:

1. An aqueous ophthalmic solution for treatment of ocular allergic conjunctivitis, the solution comprising:
   at least 0.67 w/v % olopatadine dissolved in the solution;
   PEG having a molecular weight of 300 to 500;
   polyvinylpyrrolidone;
   hydroxypropyl-γ-cyclodextrin;
   benzalkonium chloride; and
   water.

2. A solution as in claim 1 further comprising borate.

3. A solution as in claim 2 further comprising a polyol.

4. An aqueous ophthalmic solution for treatment of ocular allergic conjunctivitis, the solution comprising:
   at least 0.67 w/v % but no greater than 1.0 w/v % olopatadine dissolved in the solution;
   2.0 w/v % to 6.0 w/v % PEG having a molecular weight of 300 to 500;
   2.0 w/v % to 6.0 w/v % polyvinylpyrrolidone;
   at least 0.5 w/v % but no greater than 2.0 w/v % cyclodextrin derivative selected from the group consisting of SAE-β-cyclodextrin, HP-γ-cyclodextrin, HP-β-cyclodextrin and combinations thereof; and
   water.

5. A solution as in claim 4 further comprising borate at a concentration of at least 0.18 w/v % but less than 0.5 w/v %.

6. A solution as in claim 5 further comprising a polyol.

7. A solution as in claim 6 wherein the polyol is propylene glycol at a concentration of at least 0.4 w/v % but no greater than 2.2 w/v %.

8. An aqueous ophthalmic solution for treatment of ocular allergic conjunctivitis, the solution comprising:
   at least 0.67 w/v % but no greater than 1.0 w/v % olopatadine dissolved in the solution;
   2.0 w/v % to 6.0 w/v % PEG having a molecular weight of 300 to 500;
   2.0 w/v % to 6.0 w/v % polyvinylpyrrolidone;
   at least 0.5 w/v % but no greater than 2.0 w/v % hydroxypropyl-γ-cyclodextrin; and
   water.

9. A solution as in claim 8 further comprising borate at a concentration of at least 0.18 w/v % but less than 0.5 w/v %.

10. A solution as in claim 9 further comprising a polyol.

11. A solution as in claim 10 wherein the polyol is propylene glycol at a concentration of at least 0.4 w/v % but no greater than 2.2 w/v %.

12. A method of treating at least one ocular allergy symptom in humans, the method comprising:
topically applying to an eye of a human an amount of the solution of claim 4 sufficient to treat the at least one ocular allergy symptom.

13. A method as in claim 12 wherein the step of topically applying the solution includes dispensing at least one drop of the solution to the eye.

14. A method as in claim 13 wherein the at least one ocular allergy symptom includes ocular itching.

15. A solution as in claim 1 further comprising hydroxypropylmethyl cellulose.

16. A solution as in claim 4 further comprising at least 0.15 w/v % but no greater than 1.0 w/v % hydroxypropylmethyl cellulose.

17. A solution as in claim 8 further comprising at least 0.15 w/v % but no greater than 1.0 w/v % hydroxypropylmethyl cellulose.

18. A solution as in claim 3 wherein the polyol is mannitol.

19. A solution as in claim 6 wherein the polyol is mannitol solution at a concentration that is at least 0.05 w/v % but no greater than 0.5 w/v %.

20. A solution as in claim 10 wherein the polyol is mannitol at a concentration that is at least 0.05 w/v % but no greater than 0.5 w/v %.

21. An aqueous ophthalmic solution for treatment of ocular allergic conjunctivitis, the solution comprising:
at least 0.67 w/v % but no greater than 1.0 w/v % olopatadine dissolved in the solution;
2.0 w/v % to 6.0 w/v % PEG having a molecular weight of 300 to 500;
2.0 w/v % to 6.0 w/v % polyvinylpyrrolidone;
at least 0.5 w/v % but no greater than 2.0 w/v % hydroxypropyl-γ-cyclodextrin;
greater than 0.003 w/v % but less than 0.03 w/v % benzalkonium chloride; and
water;
wherein the pH of the solution is 6.0 to 7.8 and the osmolality of the solution is 200 to 400 mOsm/kg.

22. A solution as in claim 21 further comprising at least 0.15 w/v % but no greater than 1.0 w/v % hydroxypropylmethyl cellulose.

23. A solution as in claim 22 wherein:
i) the concentration of PEG is at least 3.0 w/v % but no greater than 5.0 w/v %;
ii) the concentration of polyvinylpyrrolidone is at least 3.0 w/v % but no greater than 5.0 w/v %; and
iii) the concentration of hydroxypropyl methylcellulose is at least 0.3 w/v % but no greater than 0.5 w/v %.

24. A solution as in claim 23 further comprising:
at least 0.18 w/v % but less than 0.4 w/v % boric acid; and
at least 0.05 w/v % but no greater than 0.5 w/v % mannitol.

25. A method of treating ocular allergy symptoms in humans, the method comprising:
topically applying to an eye of a human an amount of the solution of claim 23 sufficient to treat ocular allergy symptoms.

26. A method as in claim 25 wherein the step of topically applying the solution includes dispensing at least one drop of the solution to the eye.

27. A method as in claim 26 wherein the ocular allergy symptoms include ocular itching.

* * * * *

UNITED STATES PATENT AND TRADEMARK OFFICE
CERTIFICATE OF CORRECTION

PATENT NO. : 8,791,154 B2  
APPLICATION NO. : 13/475607  
DATED : July 29, 2014  
INVENTOR(S) : Daniel A. Gamache et al.

Page 1 of 1

It is certified that error appears in the above-identified patent and that said Letters Patent is hereby corrected as shown below:

On the Title Page:

Item (56), under References Cited, please remove --5,874,414 A 2/1999 Haseloff et al.--.

Signed and Sealed this
Fourteenth Day of October, 2014

Michelle K. Lee
*Deputy Director of the United States Patent and Trademark Office*